(12) United States Patent
Ek

(10) Patent No.: US 7,914,545 B2
(45) Date of Patent: Mar. 29, 2011

(54) SYSTEM AND METHOD FOR RETROGRADE PROCEDURE

(75) Inventor: Steven W. Ek, Bolton, MA (US)

(73) Assignee: Arthrosurface, Inc, Franklin, MA (US)

( * ) Notice: Subject to any disclaimer, the term of this patent is extended or adjusted under 35 U.S.C. 154(b) by 0 days.

(21) Appl. No.: 11/326,133

(22) Filed: Jan. 5, 2006

(65) Prior Publication Data

US 2006/0195112 A1 Aug. 31, 2006

Related U.S. Application Data

(63) Continuation-in-part of application No. 11/209,170, filed on Aug. 22, 2005, which is a continuation-in-part of application No. 11/169,326, filed on Jun. 28, 2005, which is a continuation-in-part of application No. 10/994,453, filed on Nov. 22, 2004, which is a continuation-in-part of application No. 10/308,718, filed on Dec. 3, 2002, now Pat. No. 7,163,541.

(60) Provisional application No. 60/641,552, filed on Jan. 5, 2005, provisional application No. 60/603,473, filed on Aug. 20, 2004, provisional application No. 60/583,549, filed on Jun. 28, 2004, provisional application No. 60/523,810, filed on Nov. 20, 2003.

(51) Int. Cl.
*A61B 17/32* (2006.01)

(52) U.S. Cl. .......... 606/180; 606/170; 606/172

(58) Field of Classification Search .......... 606/86–89, 606/96, 310, 313, 72–73, 79–80, 82, 84, 606/167–189; 623/22.4; 30/151–164, 329
See application file for complete search history.

(56) References Cited

U.S. PATENT DOCUMENTS

| 992,819 A | | 5/1911 | Springer |
| 1,451,610 A | | 4/1923 | Gestas |
| 2,267,925 A | * | 12/1941 | Johnston ............ 606/73 |
| 2,570,465 A | * | 10/1951 | Lundholm ............ 606/65 |
| 3,176,395 A | * | 4/1965 | Warner et al. ............ 30/154 |
| 3,600,835 A | * | 8/1971 | Hendricks ............ 43/6 |
| 3,831,585 A | * | 8/1974 | Brondy et al. ............ 600/570 |
| 3,840,905 A | | 10/1974 | Deane |
| 4,016,651 A | | 4/1977 | Kawahara et al. |

(Continued)

FOREIGN PATENT DOCUMENTS

AU 2001262308 12/2001

(Continued)

OTHER PUBLICATIONS

International Preliminary Report on Patentability dated Mar. 1, 2007 received in corresponding International Patent Application No. PCT/US2005/030120 (6 pages).

(Continued)

*Primary Examiner* — Thomas C Barrett
*Assistant Examiner* — Larry E Waggle, Jr.
(74) *Attorney, Agent, or Firm* — Grossman Tucker Perreault & Pfleger PLLC

(57) ABSTRACT

A system and method may be used for accessing an articular surface and for preparing an implant site on the articular surface. The method may include locating a portion of the articular. An access passage may be drilled towards the articular surface though bone behind the articular surface. An implant site may be excised in the articular surface relative to an axis defined by the access passage.

16 Claims, 30 Drawing Sheets

U.S. PATENT DOCUMENTS

| | | | |
|---|---|---|---|
| 4,034,418 A | 7/1977 | Jackson et al. | |
| 4,044,464 A | 8/1977 | Schiess et al. | |
| 4,158,894 A | 6/1979 | Worrell | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,712,545 A | 12/1987 | Honkanen | |
| 4,714,478 A * | 12/1987 | Fischer | 623/22.4 |
| 4,719,908 A | 1/1988 | Averill et al. | |
| 4,729,761 A | 3/1988 | White | |
| 4,788,970 A | 12/1988 | Karas et al. | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,920,958 A | 5/1990 | Walt et al. | |
| 4,927,421 A * | 5/1990 | Goble et al. | 606/73 |
| 4,938,778 A | 7/1990 | Ohyabu et al. | |
| 4,940,467 A * | 7/1990 | Tronzo | 606/66 |
| 4,946,461 A * | 8/1990 | Fischer | 606/84 |
| 4,976,037 A | 12/1990 | Hines | |
| 4,978,258 A | 12/1990 | Lins | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,092,895 A | 3/1992 | Albrektsson et al. | |
| 5,100,405 A | 3/1992 | McLaren | |
| 5,127,920 A | 7/1992 | MacArthur | |
| 5,192,291 A | 3/1993 | Pannek, Jr. | |
| 5,201,881 A | 4/1993 | Evans | |
| 5,211,647 A | 5/1993 | Schmieding | |
| 5,224,945 A | 7/1993 | Pannek, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,313,382 A | 5/1994 | Goodfellow et al. | |
| 5,314,478 A | 5/1994 | Oka et al. | |
| 5,324,295 A | 6/1994 | Shapiro | |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A | 4/1995 | Ethridge | |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,601,550 A | 2/1997 | Esser | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A | 6/1997 | Houston et al. | |
| 5,645,598 A | 7/1997 | Brosnahan, III | |
| 5,681,311 A | 10/1997 | Foley et al. | |
| 5,682,886 A | 11/1997 | Delp et al. | |
| 5,683,400 A | 11/1997 | McGuire | |
| 5,683,465 A | 11/1997 | Shinn et al. | |
| 5,683,466 A | 11/1997 | Vitale | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A | 6/1998 | Hirsch et al. | |
| 5,769,855 A | 6/1998 | Bertin et al. | |
| 5,769,899 A | 6/1998 | Hart et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,817,095 A | 10/1998 | Smith | |
| 5,824,087 A * | 10/1998 | Aspden et al. | 606/94 |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A * | 7/1999 | Mirza | 606/79 |
| 5,928,286 A | 7/1999 | Ashby et al. | |
| 5,964,752 A | 10/1999 | Stone | |
| 5,964,768 A | 10/1999 | Huebner | |
| 5,964,808 A | 10/1999 | Blaha et al. | |
| 5,968,050 A | 10/1999 | Torrie | |
| 5,989,269 A | 11/1999 | Vibe-Hansen et al. | |
| 5,990,382 A | 11/1999 | Fox | |
| 5,997,543 A | 12/1999 | Truscott | |
| 5,997,582 A * | 12/1999 | Weiss | 606/89 |
| 6,004,323 A | 12/1999 | Park et al. | |
| 6,010,502 A | 1/2000 | Bagby | |
| 6,015,411 A * | 1/2000 | Ohkoshi et al. | 606/80 |
| 6,017,348 A | 1/2000 | Hart et al. | |
| 6,019,767 A | 2/2000 | Howell | |
| 6,019,790 A | 2/2000 | Holmberg et al. | |
| 6,045,564 A | 4/2000 | Walen | |
| 6,052,909 A | 4/2000 | Gardner | |
| 6,059,831 A | 5/2000 | Braslow | |
| 6,071,310 A | 6/2000 | Picha et al. | |
| 6,081,741 A | 6/2000 | Hollis | |
| 6,086,593 A | 7/2000 | Bonutti | |
| 6,102,948 A | 8/2000 | Brosnahan, III | |
| 6,120,542 A | 9/2000 | Camino et al. | |
| 6,132,433 A | 10/2000 | Whelan | |
| 6,146,385 A | 11/2000 | Torrie et al. | |
| 6,149,654 A | 11/2000 | Lanny | |
| 6,152,960 A | 11/2000 | Pappas | |
| 6,159,216 A | 12/2000 | Burkinshaw et al. | |
| 6,168,626 B1 | 1/2001 | Hyon et al. | |
| 6,171,340 B1 | 1/2001 | McDowell | |
| 6,193,724 B1 | 2/2001 | Chan | |
| 6,206,885 B1 | 3/2001 | Ghahremani et al. | |
| 6,217,549 B1 | 4/2001 | Selmon et al. | |
| 6,251,143 B1 | 6/2001 | Schwartz et al. | |
| 6,280,474 B1 | 8/2001 | Cassidy et al. | |
| 6,299,645 B1 | 10/2001 | Ogden | |

| | | |
|---|---|---|
| 6,299,648 B1 | 10/2001 | Doubler et al. |
| 6,306,142 B1 | 10/2001 | Johanson et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1* | 3/2002 | Mirza ............................. 606/79 |
| 6,358,253 B1 | 3/2002 | Torrie et al. |
| 6,375,658 B1 | 4/2002 | Hangody et al. |
| 6,383,188 B2* | 5/2002 | Kuslich et al. ................. 606/80 |
| 6,415,516 B1 | 7/2002 | Tirado et al. |
| 6,443,954 B1* | 9/2002 | Bramlet et al. ................ 606/62 |
| 6,461,373 B2 | 10/2002 | Wyman et al. |
| 6,468,309 B1 | 10/2002 | Lieberman |
| 6,478,178 B2 | 11/2002 | Ralph et al. |
| 6,478,801 B1 | 11/2002 | Ralph et al. |
| 6,482,210 B1 | 11/2002 | Skiba et al. |
| 6,494,914 B2 | 12/2002 | Brown |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,537,274 B1 | 4/2003 | Chibrac et al. |
| 6,540,786 B2 | 4/2003 | Chibrac et al. |
| 6,551,322 B1 | 4/2003 | Lieberman |
| 6,554,866 B1 | 4/2003 | Aicher et al. |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,984,248 B2 | 7/2003 | Hyde, Jr. |
| 6,607,561 B2* | 8/2003 | Brannon .................... 623/23.11 |
| 6,610,067 B2 | 8/2003 | Tallarida |
| 6,626,950 B2 | 9/2003 | Brown et al. |
| 6,679,917 B2 | 1/2004 | Ek |
| 6,746,451 B2* | 6/2004 | Middleton et al. .............. 606/79 |
| 6,755,837 B2 | 6/2004 | Ebner |
| 6,783,550 B2 | 8/2004 | MacArthur |
| 6,802,864 B2 | 10/2004 | Tornier |
| 6,814,734 B2* | 11/2004 | Chappuis et al. ............... 606/80 |
| 6,814,735 B1 | 11/2004 | Zirngibl |
| 6,827,722 B1 | 12/2004 | Schoenefeld |
| 6,860,902 B2 | 3/2005 | Reiley |
| 6,884,246 B1 | 4/2005 | Sonnabend et al. |
| 6,893,467 B1 | 5/2005 | Bercovy |
| 6,923,813 B2* | 8/2005 | Phillips et al. .................. 606/86 |
| 6,926,739 B1 | 8/2005 | OConnor |
| 6,962,577 B2 | 11/2005 | Tallarida et al. |
| 6,969,393 B2 | 11/2005 | Pinczewski et al. |
| 6,989,016 B2 | 1/2006 | Tallarida et al. |
| 7,029,479 B2 | 4/2006 | Tallarida |
| 7,063,717 B2 | 6/2006 | St. Pierre et al. |
| 7,115,131 B2 | 10/2006 | Engh et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,204,839 B2 | 4/2007 | Dreyfuss et al. |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 6,783,551 B1 | 11/2007 | Metzger |
| 7,290,347 B2 | 11/2007 | Augostino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,510,558 B2 | 3/2009 | Tallarida |
| 7,569,059 B2 | 8/2009 | Cerundolo |
| 7,641,658 B2* | 1/2010 | Shaolian et al. ................ 606/80 |
| 2001/0012967 A1 | 8/2001 | Mosseri |
| 2001/0034526 A1* | 10/2001 | Kuslich et al. .................. 606/80 |
| 2001/0039455 A1 | 11/2001 | Simon et al. |
| 2001/0056266 A1 | 12/2001 | Tallarida et al. |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0147498 A1 | 10/2002 | Tallarida et al. |
| 2003/0028196 A1 | 2/2003 | Bonutti |
| 2003/0060887 A1 | 3/2003 | Ek |
| 2003/0065391 A1* | 4/2003 | Re et al. ..................... 623/13.14 |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0171756 A1 | 9/2003 | Fallin et al. |
| 2003/0181878 A1 | 9/2003 | Tallarida et al. |
| 2003/0204195 A1 | 10/2003 | Keane et al. |
| 2003/0216669 A1 | 11/2003 | Lang et al. |
| 2003/0216742 A1* | 11/2003 | Wetzler et al. .................. 606/96 |
| 2003/0225456 A1 | 12/2003 | Ek |
| 2003/0225457 A1 | 12/2003 | Justin et al. |
| 2004/0015170 A1 | 1/2004 | Tallarida et al. |
| 2004/0034359 A1 | 2/2004 | Schmieding et al. |
| 2004/0034437 A1 | 2/2004 | Schmieding |
| 2004/0082906 A1 | 4/2004 | Tallarida et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0193281 A1 | 9/2004 | Grimes |
| 2004/0199166 A1 | 10/2004 | Schmieding et al. |
| 2004/0210209 A1 | 10/2004 | Denzer et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043805 A1 | 2/2005 | Chudik |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0154398 A1 | 7/2005 | Miniaci et al. |
| 2005/0209705 A1 | 9/2005 | Niederauer et al. |
| 2005/0229323 A1 | 10/2005 | Mills et al. |
| 2005/0287187 A1 | 12/2005 | Mansmann |
| 2006/0004461 A1 | 1/2006 | Justin et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058883 A1 | 3/2006 | Aram et al. |
| 2006/0085006 A1 | 4/2006 | Ek |
| 2006/0149370 A1 | 7/2006 | Schmieding et al. |
| 2006/0184171 A1* | 8/2006 | Surti ............................. 606/170 |
| 2006/0190002 A1 | 8/2006 | Tallarida |
| 2006/0229726 A1 | 10/2006 | Ek |
| 2007/0005143 A1 | 1/2007 | Ek |
| 2007/0029951 A1 | 2/2007 | Schmieding |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093890 A1 | 4/2007 | Eliasen et al. |
| 2007/0118136 A1 | 5/2007 | Ek |
| 2007/0123921 A1 | 5/2007 | Ek |
| 2007/0179608 A1 | 8/2007 | Ek |
| 2007/0233128 A1 | 10/2007 | Schmieding et al. |
| 2007/0250067 A1 | 10/2007 | Schmieding et al. |
| 2007/0255399 A1 | 11/2007 | Eliasen et al. |
| 2007/0265700 A1 | 11/2007 | Eliasen et al. |
| 2007/0288803 A1 | 12/2007 | Dreyfuss et al. |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0086139 A1 | 4/2008 | Bourke et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0275512 A1 | 11/2008 | Albertorio et al. |
| 2008/0306483 A1 | 12/2008 | Iannarone |

| 2009/0198288 A1 | 8/2009 | Hoof et al. |
| 2009/0234452 A1 | 9/2009 | Steiner et al. |
| 2009/0275950 A1 | 11/2009 | Sterrett et al. |

FOREIGN PATENT DOCUMENTS

| | | |
|---|---|---|
| AU | 2003262428 | 8/2009 |
| DE | 2933174 | 4/1980 |
| DE | 3516743 | 11/1986 |
| DE | 3840466 | 6/1990 |
| EP | 0241240 | 10/1987 |
| EP | 0350780 | 1/1990 |
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 20040026170 | 4/2004 |
| WO | 2004052216 | 6/2004 |
| WO | 2004075777 | 9/2004 |
| WO | 2005051231 | 6/2005 |
| WO | 20050512331 | 6/2005 |
| WO | 20060004885 | 1/2006 |
| WO | 20060091686 | 8/2006 |

OTHER PUBLICATIONS

International Search Report with Written Opinion dated Nov. 29, 2006 received in corresponding International Patent Application No. PCT/US05/23200 (7 pages).

International Search Report with Written Opinion dated Nov. 27, 2006 received in corresponding International Patent Application No. PCT/US06/00380 (8 pages).

Atos News, Oct. 2005, "The Artificial Limb "Eclipse"—A new draft without shank in the implantation of artificial shoulder limbs", cover page with pp. 40-41, with English translation dated Jan. 13, 2006 (5 pages).

Suganuma, et al., "Arthroscopically Assisted Treatment of Tibial Plateau Fractures", The Journal of Arthroscopic and Related Surgery, vol. 20 No. 10, Dec. 2004, pp. 1084-1089 (6 pages).

Siguier, et al., "Preliminary Results of Partial Surface Replacement of the Femoral Head in Osteonecrosis", The Journal of Arthroplasty, vol. 14 No. 1, 1999, pp. 45-51 (7 pages).

Siguier, et al., "Partial Resurfacing Arthroplasty of the Femoral Head in Avascular Necrosis", Clinical Orthopaedics and Related Research, No. 386, 2001, pp. 85-92 (5 pages).

EPO Search Report received in related EPO Application No. 03 026 286.9 dated Apr. 27, 2004 (6 pages).

EPO Office Action dated Aug. 23, 2004, received in related EPO Application No. 03 026 286.9 (4 pages).

EPO Office Action dated Mar. 15, 2005, received in related EPO Application No. 03 026 286.9 (3 pages).

EPO Examination Report dated Feb. 22, 2005, received in related EPO Application No. 01 932 833.5 (3 pages).

International Search Report with Written Opinion dated Jan. 30, 2006, received in related PCT Application No. PCT/US04/39181 (6 pages).

Notice of Allowance issued in corresponding U.S. Appl. No. 10/618,887 dated Sep. 13, 2007.

International Preliminary Report on Patentability and Written Opinion dated May 22, 2006 in corresponding PCT patent application No. PCT/US04/039181.

English language translation of Japanese Office Action dated Aug. 9, 2007 issued in corresponding Japanese application No. 2003-552148.

Canadian Office Action dated Jan. 2, 2008 issued in corresponding Canadian Application No. 2407440.

International Preliminary Report on Patentability and Written Opinion dated Jun. 28, 2007 in corresponding PCT patent application No. PCT/US2005/005980.

International Preliminary Report on Patentability and Written Opinion dated Jul. 19, 2007 in corresponding PCT patent application No. PCT/US2006/000380.

International Search Report dated Dec. 27, 2001 issued in corresponding PCT patent application No. PCT/US01/14061.

International Search Report dated May 23, 2003 issued in corresponding PCT patent application No. PCT/US02/40310.

International Search Report and Written Opinion dated Dec. 30, 2004 issued in corresponding PCT patent application No. PCT/US04/05539.

International Search Report and Written Opinion dated Aug. 30, 2006 issued in corresponding PCT patent application No. PCT/US06/06323.

International Search Report and Written Opinion dated May 22, 2007 issued in corresponding PCT patent application No. PCT/US05/05980.

International Search Report and Written Opinion dated Aug. 8, 2007 issued in corresponding PCT patent application No. PCT/US06/29875.

Notice of Allowance issued in corresponding U.S. Appl. No. 10/308,718 dated Sep. 11, 2006.

Office Action issued in corresponding U.S. Appl. No. 10/741,044 dated Oct. 26, 2005.

USPTO Office Action dated Dec. 21, 2007 issued in corresponding U.S. Appl. No. 11/169,326.

USPTO Office Action dated Dec. 26, 2007 issued in U.S. Appl. No. 11/379,151.

USPTO Office Action dated Oct. 9, 2007 issued in U.S. Appl. No. 10/373,463.

USPTO Office Action dated Aug. 29, 2007 issued in U.S. Appl. No. 10/760,965.

USPTO Office Action dated Apr. 26, 2007 issued in U.S. Appl. No. 10/373,463.

USPTO Office Action dated Apr. 4, 2007 issued in corresponding U.S. Appl. No. 10/789,545.

USPTO Office Action dated Mar. 15, 2007 issued in U.S. Appl. No. 10/760,965.

USPTO Office Action dated Nov. 6, 2006 issued in U.S. Appl. No. 10/760,965.

USPTO Office Action dated Oct. 17, 2006 issued in U.S. Appl. No. 10/373,463.

USPTO Office Action dated Oct. 31, 2006 issued in U.S. Appl. No. 10/760,965.

USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09846657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Search Report received in related EPO Application No. 03 02 6286.9 dated Feb. 26, 2004 (5pgs).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.

Thermann, et al, ATOS Newsletter, Jun. 2005, Aktuelle Thennen, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product_det_prn& tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Bale, MD, Reto J., et al, "Osteochondral Lesions of the Talus: Computer-assisted Retrograde Drilling Feasibility and Accuracy in Initial Experriences[1]", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al 'Arthroscopic Drilling for the Treatment of Osteochondral Lesions of the Talus[*], The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug.), 2001:pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Arnette Blackwell SA.

Taranow WS, et al, "Retrograde drilling of osteochondral lesions of the medial talar dome", PubMed, www.pubmed.gov, A service of the National Library of Medicing and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.

U.S. Office Action dated Oct. 21, 2008 issued in related U.S. Appl. No. 11/461,240.

U.S. Office Action dated Jun. 25, 2008 issued in related U.S. Appl. No. 11/359,891.

Habermeyer, "Eclipse, Schaftfreie Schulterprothese Operationsanleitung," (dated unknown).

U.S. Office Action dated Jul. 2, 2008 issued in related U.S. Appl. No. 11/379,151.

European Office Action dated Oct. 6, 2008 issued in related European Patent Application No. 01932833.5-2310.

U.S. Office Action dated Jun. 27, 2008 issued in related U.S. Appl. No. 10/760,965.

International Search Report and Written Opinion dated Oct. 1, 2008 issued in related International Patent Application No. PCT/US08/53194.

International Search Report and Written Opinion dated Oct. 9, 2008 issued in related International Patent Application No. PCT/US07/82262.

European Search Report dated Nov. 4, 2008 issued in related European Patent Application No. 04811836.8-2310.

U.S. Office Action dated Jan. 9, 2009 issued in related U.S. Appl. No. 10/373,463.

Canadian Office Action dated Dec. 9, 2008 issued in related Canadian Patent Application No. 2407440.

Supplemental European Search Report dated Nov. 6, 2008 issued in related European Patent Application No. 05791453.3-2310.

Japanese Office Action dated Dec. 19, 2008 issued in Japanese Patent Application No, 2006501193.

Japanese Office Action dated Jan. 13, 2009 issued in Japanese Patent Application No, 2003552147.

International Search Report dated Jan. 30, 2006 issued in related International Patent Application No. PCT/US04/39181.

U.S. Office Action dated Mar. 27, 2009 issued in related U.S. Appl. No. 11/169,326.

European Office Action dated Feb. 26, 2009 in related European Patent Application No. 05791453.3.

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 ages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Arthroplasty," Foot Ankle Clin. N. Am. 14 (2009) pp. 33-42.

Cook, et al., "Meta-analysis of First Metatarsophalangeal Joint Implant Arthroplasty," Journal of Foot and Ankle Surgery, vol. 48, Issue 2, pp. 180-190 (2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1): 56-63.

United States Office Action dated May 13, 2009 issued in related U.S. Appl. No. 11/359,892.

United States Office Action dated May 18, 2009 issued in related U.S. Appl. No. 11/209,170.

United States Office Action dated May 1, 2009 issued in related U.S. Appl. No. 11/461,240.

Australian Office Action dated Jan. 29, 2009 issued in related Australian Patent Application No. 2004216106.

European Search Report dated Apr. 22, 2009 issued in related European Patent Application No. 09002088.4.

U.S. Office Action dated Aug. 30, 2006 issued in related U.S. Appl. No. 10/618,887.

U.S. Office Action dated Jan. 15, 2008 issued in related U.S. Appl. No. 10/618,887.

U.S. Office Action dated May 18, 2009 issued in related U.S. Appl. No. 11/209,170.

U.S. Office Action dated May 28, 2009 issued in related U.S. Appl. No. 11/359,891.

U.S. Office Action dated May 13, 2009 issued in related U.S. Appl. No. 11/359,892.

International Search Report and Written Opinion dated Jun. 1, 2009 issued in related International Patent Application No. PCT/US2009/035889.

International Preliminary Report and Patentability dated May 7, 2009 issued in related International Patent Application No. PCT/US2007/082262.

Supplemental European Search Report dated May 28, 2009 issued in related International European Patent Application No. 01997077.1.

Supplemental European Search Report dated May 11, 2009 issued in related International European Patent Application No. 02805182.9.

Notice of Allowance dated Feb. 20, 2009 issued in related U.S. Appl. No. 10/618,887.

Notice of Reasons for Rejection issued in related Japanese Patent Application No. 2003-394702 mailed Jul. 21, 2009.

Notice of Reasons for Rejection issued in related Japanese Patent Application No. 20-541615 mailed May 26, 2009.

International Preliminary Report on Patentability issued in related Patent Application No. PCT/US2007/025284 dated Jun. 25, 2009.

Office Action issued in related Australian Patent Application No. 2007216648 dated Jul. 28, 2009.

European Search Report dated Jul. 10, 2009 issued in related European Patent Application No. 09002088.4.

United States Office Action issued is related U.S. Appl. No. 10/760,965 dated Feb. 19, 2008.

Australian Office Action issued in related Australian Patent Application No. 2003262428 dated Mar. 20, 2008.

Australian Office Action issued in related Australian Patent Application No. 2004293042 dated Feb. 20, 2008.

International Search Report and Written Opinion dated Jun. 24, 2008 issued in related International Patent Application No. PCT/US07/73685.

International Search Report and Written Opinion dated Jun. 11, 2008 issued in related International Patent Application No. PCT/US07/25284.

International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related European Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
Notice of Reasons for Rejection dated Nov. 17, 2009 issued in Japanese Patent Application No. 2007-519417.
European Search Report dated Dec. 3, 2009 issued in related European Patent Application No. 06735827.5.
Supplemental Notice of Allowance dated Nov. 25, 2009 issued in related U.S. Appl. No. 10/373,463.
Office Action dated Dec. 24, 2009 issued in related U.S. Appl. No. 10/994,453.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Aug. 27, 2009 issued in related U.S. Appl. No. 10/760,965.
Notice of Allowance dated Oct. 9, 2009 issued in related U.S. Appl. No. 10/373,463.
Australian Office Action dated Oct. 29, 2009 issued in related Australian Patent Application No. 2007203623.
Notice of Allowance dated Aug. 25, 2009 issued in related U.S. Appl. No. 11/379,151.
Japanese Notice of Reasons for Rejection dated Sep. 8, 2009 issued in related Japanese Patent Application No. 2003552147.
European Office Action dated Jan. 11, 2010 issued in related European Patent Application No. 2005218302.
U.S. Office Action dated Mar. 9, 2010 issued in related U.S. Appl. No. 11/359,892.
Supplemental Notice of Allowance dated Feb. 2, 2010 issued in related U.S. Appl. No. 10/373,463.
U.S. Office Action dated Mar. 2, 2010 issued in related U.S. Appl. No. 11/169,326.
Australian Office Action dated Apr. 9, 2010 issued in related Australian Patent Application No. 2005260590.
European office communication dated Feb. 10, 2010 issued in related European Patent Application No. 09002088.4-2310.
Australian Office Action dated Feb. 26, 2010 issued in related Australian Patent Application No. 2008207536.

U.S. Office Action dated Mar. 9, 2010 issued in related U.S. Appl. No. 11/359,892.
Supplemental Notice of Allowance dated Feb. 2, 2010 issued in related U.S. Appl. No. 10/373,463.
U.S. Office Action dated Mar. 2, 2010 issued in related U.S. Appl. No. 11/169,326.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European office communication dated Apr. 13, 2010 issued in related European Patent Application No. 02805182.9-2310.
European office communication dated Mar. 25, 2010 issued in related European Patent Application No. 01997077.1-2310.
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May. 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Notice of Allowance dated Aug. 6, 2010 issued in related U.S. Appl. No. 11/359,892.
International Preliminary Report on Patentability dated Sep. 16, 2010 issued in related International Patent Application No. PCT/US2009/035889.
Office Action dated Oct. 11, 2010 issued in related Australian Patent Application No. 2006216725.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.

* cited by examiner

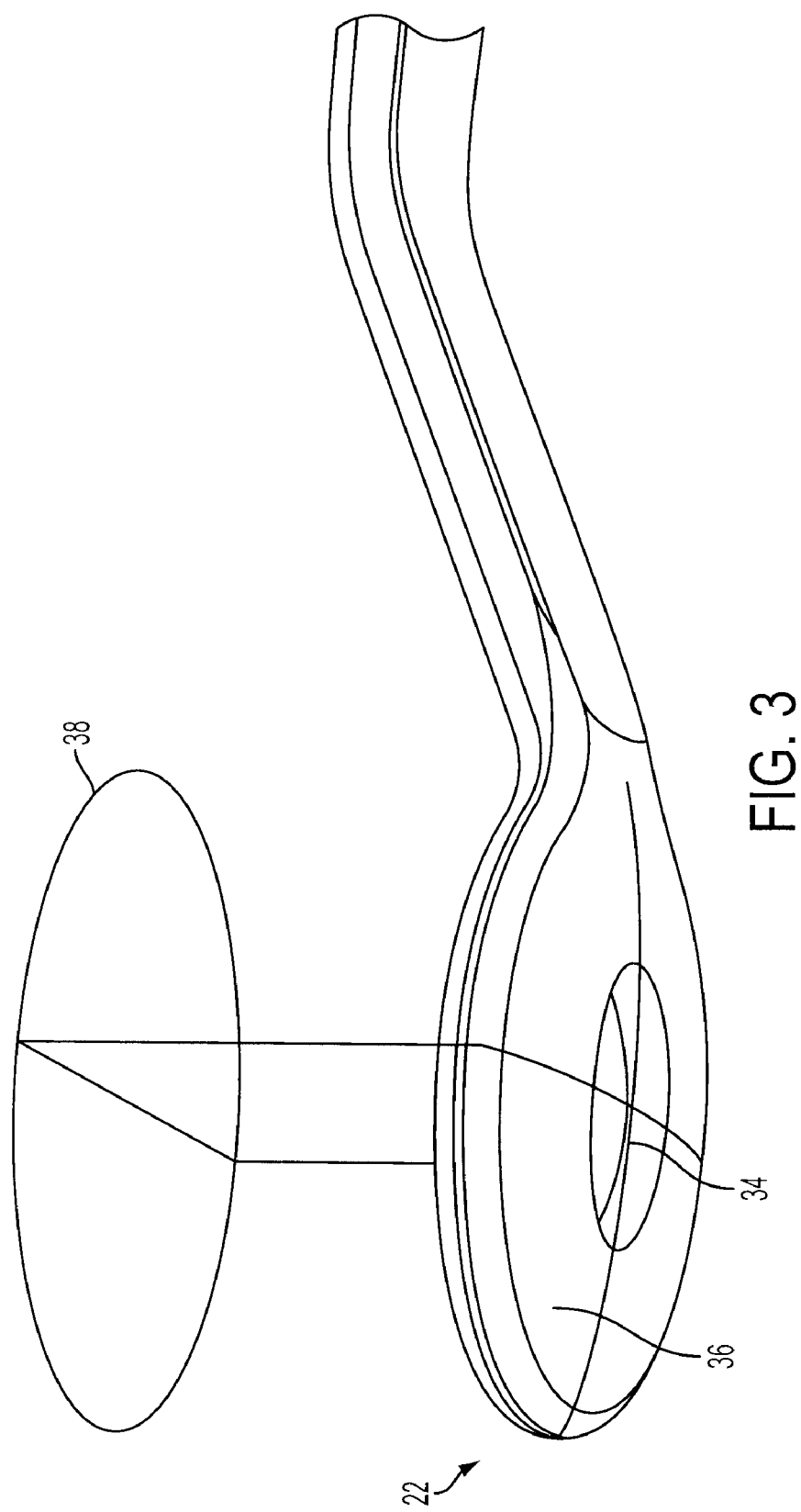

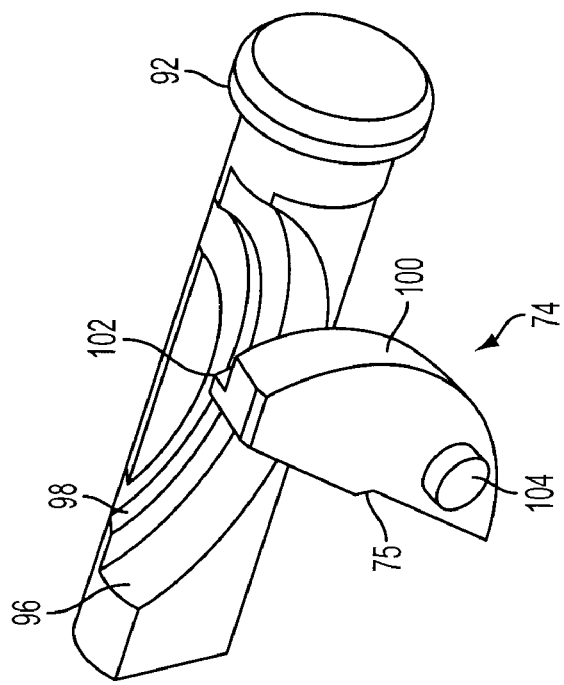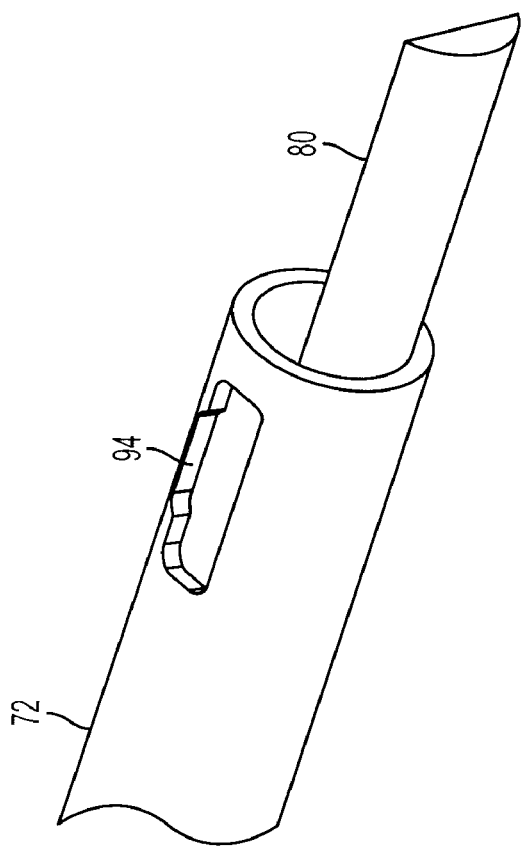
FIG. 11

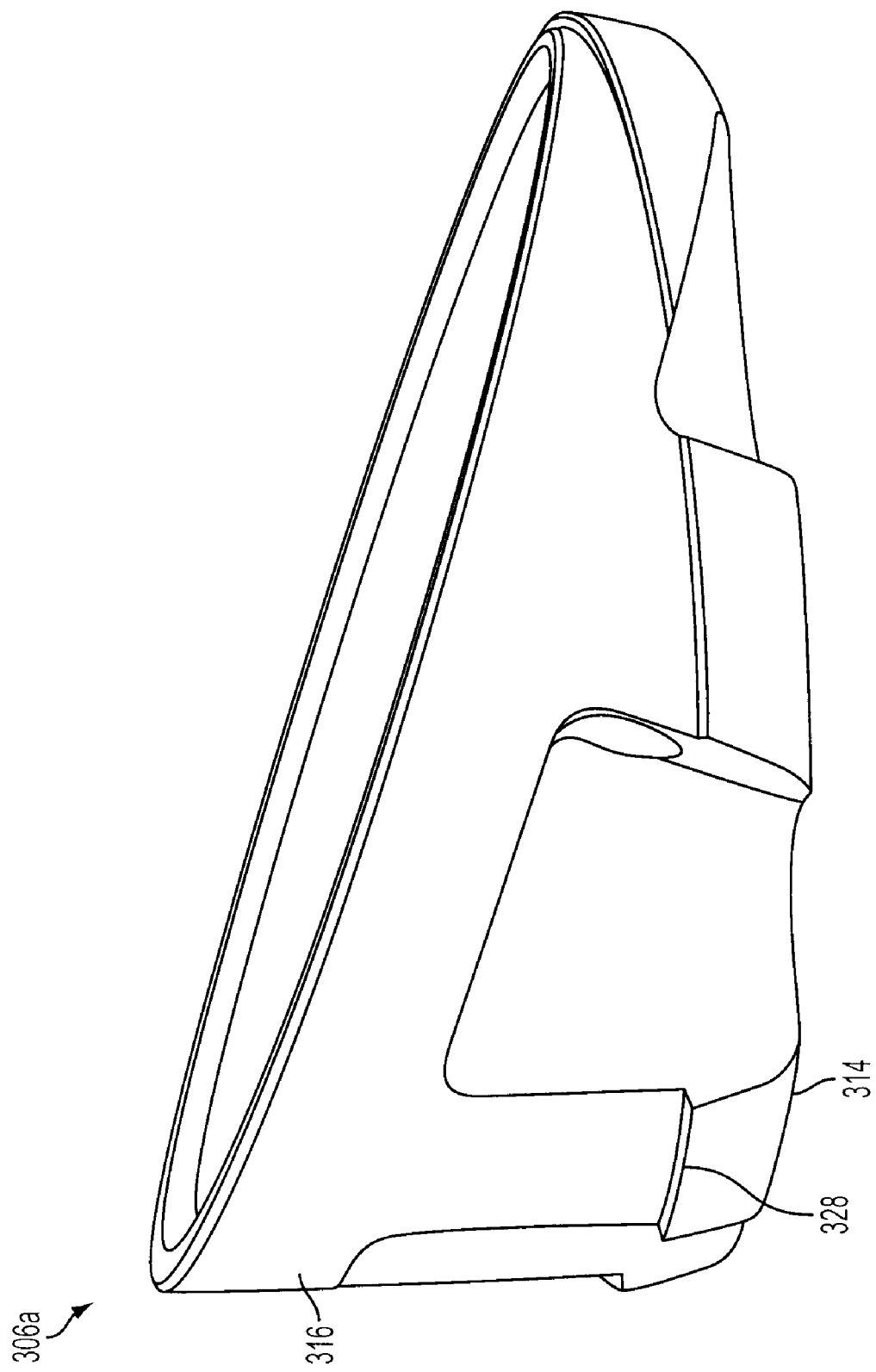

SYSTEM AND METHOD FOR RETROGRADE PROCEDURE

CROSS-REFERENCE TO RELATED APPLICATIONS

This application claims the Benefit of U.S. provisional patent application Ser. No. 60/641,552, filed Jan. 5, 2005. This application is also a continuation-in-part of U.S. patent application Ser. No. 11/209,170, filed Aug. 22, 2005, which claims the benefit of U.S. provisional patent application Ser. No. 60/603,473, filed Aug. 20, 2004. This application is also a continuation in part of U.S. patent application Ser. No. 11/169,326, filed Jun. 28, 2005, which claims the benefit of U.S. provisional patent application Ser. No. 60/583,549, filed Jun. 28, 2004. This application is also a continuation in part of U.S. patent application Ser. No. 10/994,453, filed Nov. 22, 2004, which claims the benefit of U.S. provisional patent application Ser. No. 60/523,810, filed Nov. 20, 2003. Additionally, this application is also a continuation in part of U.S. patent application Ser. No. 10/308,718, filed Dec. 3, 2002 now U.S. Pat. No. 7,163,541. Then entire disclosures of all of the above listed applications are incorporated herein by reference.

FIELD

The present disclosure is directed at a system and method for accessing an articular joint surface. The present disclosure is further directed at a method and system for replacing at least a portion of an articular surface.

BACKGROUND

Articular cartilage, found at the ends of articulating bone in the body, is typically composed of hyaline cartilage, which has many unique properties that allow it to function effectively as a smooth and lubricious load bearing surface. Hyaline cartilage problems, particularly in knee, hip joints, and should joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and eventually, loss of joint movement. As a result, various methods have been developed to treat and repair damaged or destroyed articular cartilage.

For smaller defects, traditional options for this type of problem include leaving the lesions or injury alone and living with it, or performing a procedure called abrasion arthroplasty or abrasion chondralplasty. The principle behind this procedure is to attempt to stimulate natural healing. The bone surface is drilled using a high speed rotary burr or shaving device and the surgeon removes about 1 mm of bone from the surface of the lesion. This creates an exposed subchondral bone bed that will bleed and will initiate a fibrocartilage healing response. One problem with this procedure is that the exposed bone is not as smooth as it originally was following the drilling and burring which tends to leave a series of ridges and valleys, affecting the durability of the fibrocartilage response. Further, although this procedure can provide good short term results, (1-3 years), fibrocartilage is seldom able to support long-term weight bearing and is prone to wear, soften and deteriorate.

Another procedure, called Microfracture incorporates some of the principles of drilling, abrasion and chondralplasty. During the procedure, the calcified cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique may be expected to be similar to abrasion chondralplasty. Another means used to treat damaged articular cartilage is a cartilage transplant. Essentially, this procedure involves moving cartilage from an outside source or other knee or from within the same knee into the defect. Typically, this is done by transferring a peg of cartilage with underlying bone and fixing it in place with a screw or pin or by a press fit. Although useful for smaller defects, large defects present a problem, as this procedure requires donor pegs proportionate to the recipient bed. Large diameter lesions may exceed the capacity to borrow from within the same knee joint and rule out borrowing from another source.

Larger defects, however, generally require a more aggressive intervention. Typically treatment requires replacing a portion or all of the articular surface with an implant or prosthetic having an outer layer that that is polished or composed of a material that provides a lubricious load bearing surface in approximation of an undamaged cartilage surface. Replacement of a portion, or all, of the articular surface requires first cutting, boring, or reaming the damaged area to remove the damaged cartilage. A recess to receive an implant or prosthetic is formed at the damaged site. The implant or prosthetic is then secured to the bone in an appropriate position in the recess.

The treatment and/or replacement procedure often requires direct access to the damaged surface of the cartilage. While the most commonly damaged portions of some joints may easily be accessed for repair using a minimally invasive procedure some joints are not nearly as accessible. For example, the superior or medial femoral head, the medial humeral head, the glenoid, etc. do not permit direct access sufficient to carry out replacement of the articular surface in a minimally invasive manner. In fact, repair of such obstructed joints often requires an invasive procedure and necessitates complete dislocation of the joint. Procedures of such an invasive nature may be painful and require an extended recovery period.

Accordingly, it is an object of the present disclosure to provide a method for replacing an articular joint surface that is obscured from axial approach that is less invasive than conventional procedures and may not necessitate completely dislocating the joint.

BRIEF DESCRIPTION OF THE DRAWINGS

Features and advantages of the present invention are set forth by description of embodiments consistent therewith, which description should be considered in combination with the accompanying drawings, wherein:

FIG. 3 is a detailed view of an aiming tip of an aiming member consistent with the present disclosure;

FIG. 11 is a detailed exploded view of a distal end of an excision device consistent with the present disclosure including a cutter;

FIG. 29 is a perspective view of a lower component of an articular surface implant consistent with the present disclosure.

DESCRIPTION

By way of overview, the present disclosure provides a retrograde articular surface replacement system that may include a method and apparatus for replacing at least a portion of an articular surface, including accessing a portion of the articular surface through a portion of bone. While the preceding overview and the following embodiments of a system according to the present disclosure are directed at a system for replacing at least a portion of an articular surface, the system herein may be used in connection with procedures other than the replacement of portions of an articular surface. From a broad standpoint, the system disclosed herein may provide an apparatus and method for accessing a bone, joint, etc., indirectly.

Figure 1:
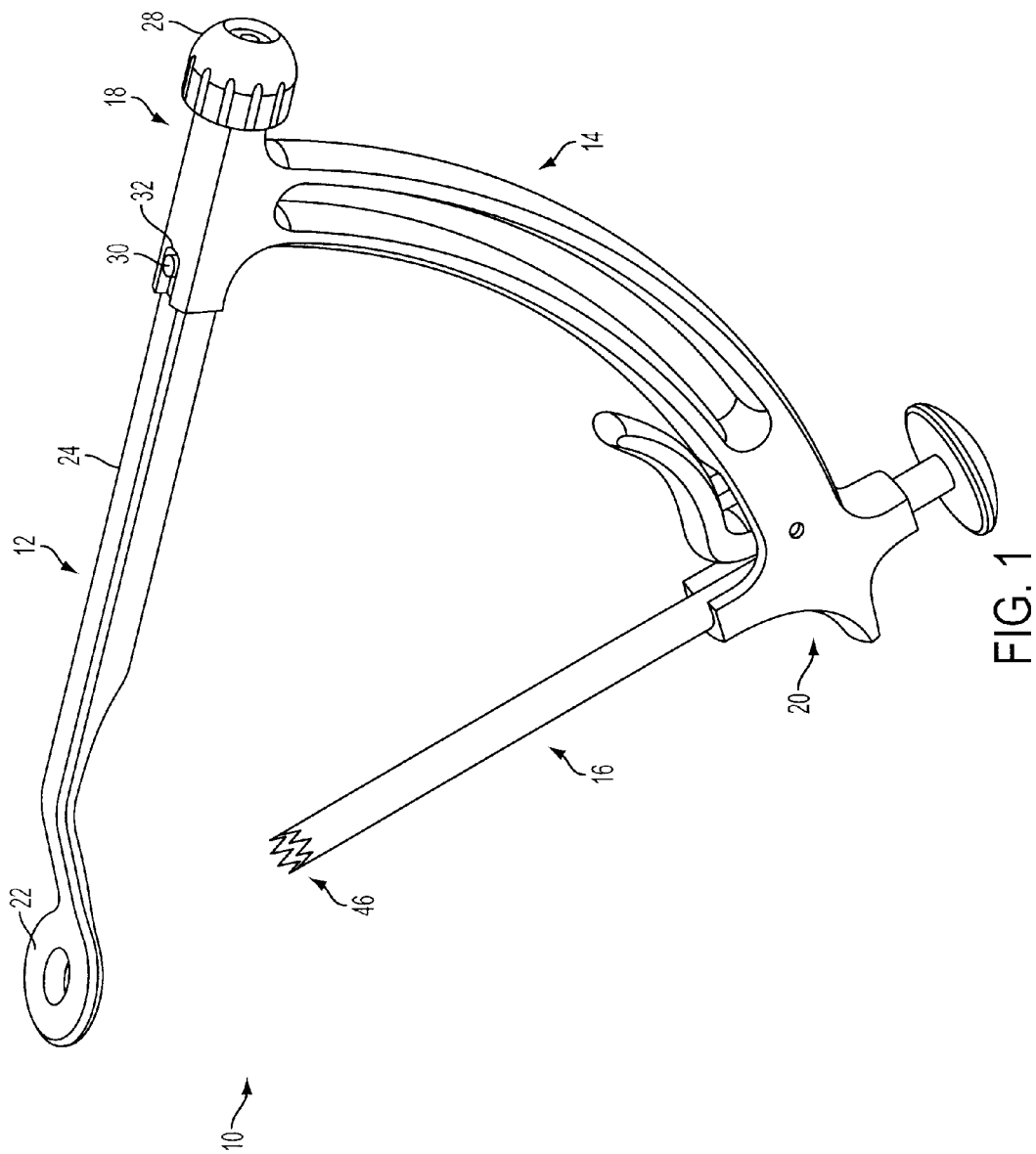
FIG. 1 is a perspective view of an embodiment of a drill guide consistent with the present disclosure.

Referring to FIG. 1, an embodiment of a drill guide system 10 consistent with the preset disclosure is shown. The drill guide system 10 may generally include an aiming member 12, a frame 14, and a cannulated shaft 16. The aiming member 12 may be removably coupled to the frame 14 at a first end 18 of the frame 14. Similarly, the cannulated shaft 16 may be coupled to and/or may be releasably engaged to the frame 14 at a second end 20 of the frame 14. The frame 14 may arrange the aiming assembly 12 and the cannulated shaft 16 in an angular and/or positional relationship to one another.

Figure 2:
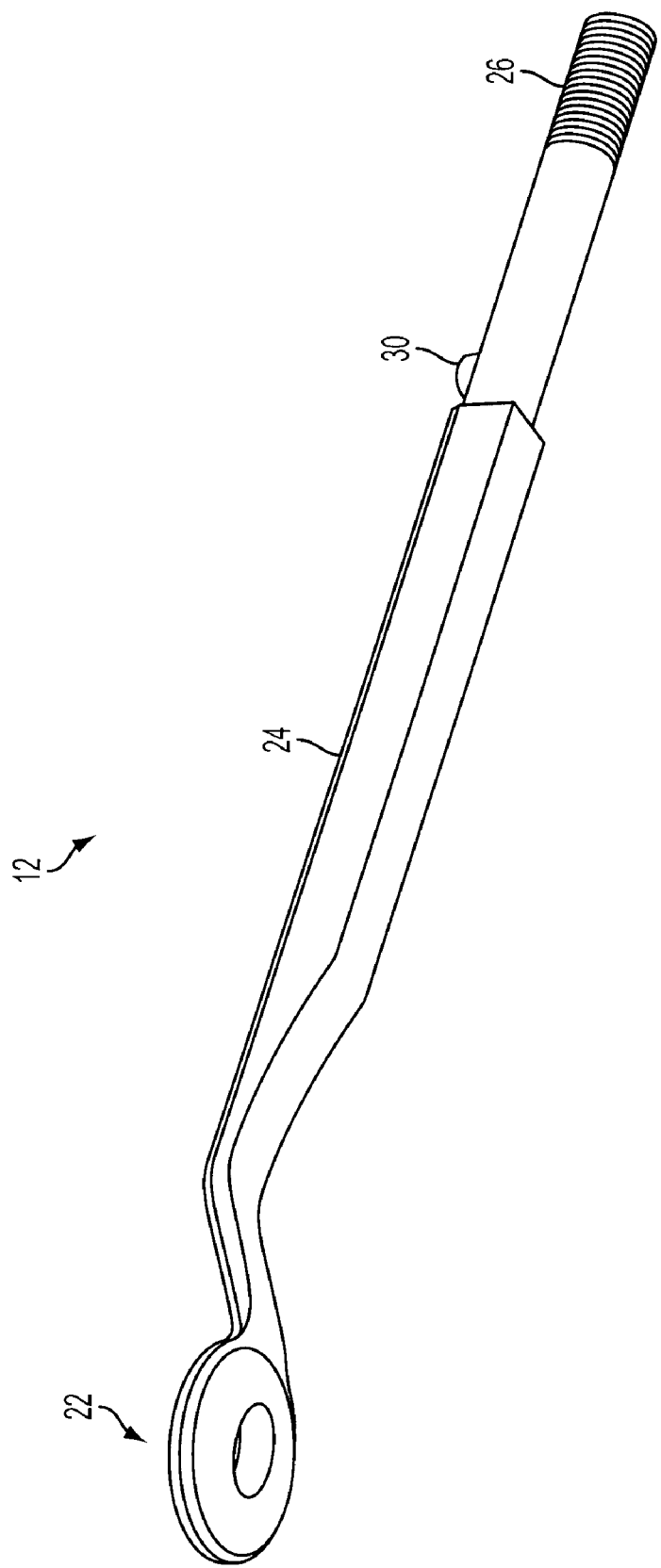
FIG. 2 shows an embodiment of a modular aiming member consistent with the present disclosure in perspective view.

The aiming member 12 may generally include an aiming tip 22 disposed at a distal end of an arm 24. With additional reference to FIG. 2, the aiming member 12 may be a modular component that may be removably coupled to the frame 14. According to an embodiment, the proximal end of the arm 24 may include a threaded portion 26 for removably coupling the aiming member 12 to the frame 14. The threaded portion 26 of the aiming member 12 may be received through a cooperating opening in the first end 18 of the frame 14. The aiming member 12 may be secured to the frame 14 using a knob 28 that may be threadably engaged to the threaded portion 26 of the aiming member 12. The aiming member 12 may include a protrusion 30 that may be received in a cooperating cutout 32 in the frame 14. The protrusion 30 and cooperating cutout 32 may provide any of a variety of functions. For example, the cooperating protrusion 30 and cutout 32 may orient the aiming tip 22 rotationally about the axis of the arm 24 relative to the frame 14. In this manner, the engagement of the protrusion 30 in the cooperating cutout 32 may maintain the aiming member 12, and thereby the aiming tip 22, in a particular rotational orientation relative to the frame 24. Additionally, the protrusion 30 may aid in locating the aiming member 12 relative to the frame 14. Specifically, the extension of the aiming tip 22 from the frame 14 may, therefore, be fixed by the engagement of the protrusion 30 in the cutout 32. With the protrusion 30 disposed in the cutout 32, the aiming member 12 may be drawn toward the frame 14 by the threaded engagement between the threaded portion of the aiming member 12 and the knob 28 until the protrusion bottoms out in the cutout 32. In this manner, the aiming tip 22 may be disposed a distance from the frame 14 based on the location of the cutout 32 and the distance between the protrusion 30 and the aiming tip 22.

Referring to FIG. 3, the aiming tip 22 is shown in detail. As illustrated, the aiming tip 22 may have a slim profile, i.e., a relatively small thickness. The slim profile of the aiming tip 22 may facilitate positioning the aiming tip 22 within a joint while minimizing the need to dislocate or separate the joint. The slim profile may, therefore, minimize the invasiveness and/or the ancillary damage caused by a procedure utilizing the drill guide 10.

As depicted in the illustrated embodiment, the aiming tip 22 of the aiming member 12 may include an opening 34 extending through the aiming tip 22. The opening 34 may allow the aiming tip 22 to be positioned proximate a defect in an articular surface and/or a proximate to a determinable location on the articular surface. Positioning of the aiming tip 22 may be ascertained arthroscopically. Accordingly, it may be possible to generally and/or precisely locate or center the aiming tip 22 about a location on an articular surface using a visual reference on the articular surface.

The aiming tip 22 may have a projected geometry 38 that may correspond to the projected geometry of a load bearing surface of an articular surface implant. Accordingly, the aiming tip 22 may be employed in the manner of a trial gauge to determine the size of an articular surface implant necessary to replace a damaged or defective region of the articular surface. The necessary size of an articular surface implant may be determined by sequentially positioning a series of modular aiming features 12 within the joint. Each of the series of aiming features 12 may include an aiming tip 22 having different projected areas. In this manner, a desired size of an articular surface implant may be ascertained by visual inspection. As indicated above, visual inspection may be carried out arthroscopically.

Similarly, the aiming tip 22 of the aiming member 12 may be used as a trial gauge for at least generally measuring and/or determining the contour of at least a portion of the articular surface. A set of aiming members 12 may be provided including aiming tips 22 each having a contacting surface 36 having a different geometry or contour. Aiming members 12 including aiming tips 22 with different geometry or contour contacting surfaces 36 may be sequentially positioned on the articular surface. The degree of fit between the contacting surface 36 of each aiming tip 22 and the articular surface may be visually ascertained and/or ascertained based at least in part on tactile feedback. Regarding the latter, tactile feedback corresponding to the degree of fit between the aiming tip 22 and the articular surface may, for example, be based on the degree or amount of wobble of the aiming tip 22 when the aiming tip 22 is positioned on the articular surface. Alternative methods for ascertaining the degree of fit between the aiming tip 22 and the articular surface may also be employed. For example, various imaging techniques, e.g. radioscopic imaging, may be used to determine the fit between the aiming tip 22 and the articular surface.

Consistent with the foregoing, the aiming tip 22 may be used in a manner similar to a feeler gauge, or trial gauge, to determine the size of an implant to replace a defect etc. in an articular surface and/or to determine the geometry or contour of the articular surface in the region of the articular surface to be replaced. An implant may be produced having a size and load bearing surface geometry that is based on, and/or the compliment of, the size and/or geometry or contour of the articular surface as determined using the modular aiming tips 22. Alternatively, an implant, having a desired size and load bearing surface geometry or contour, based on the determined size and/or geometry or contour of the region of the articular surface to be replaced, may be selected from a set of implants having a variety of sizes and/or surface geometries or contours.

While the preceding implementation of the aiming tip 22 contemplates determining both the size and the geometry or contour of a portion of an articular surface to be replaced, the aiming tip 22 herein may alternatively be employed to determine only one of the size and the geometry of a portion of an articular surface to be replaced. For example, all of the modular aiming members 12 may be provided including aiming tips having the same projected area or size, and differing only in the geometry or contour of the contacting surface 36. Furthermore, the aiming member 12 need not be used to accomplish any measuring or estimating processes. Rather, the aiming member 12 may by used only to locate a desired region on the articular surface.

Figure 3B:
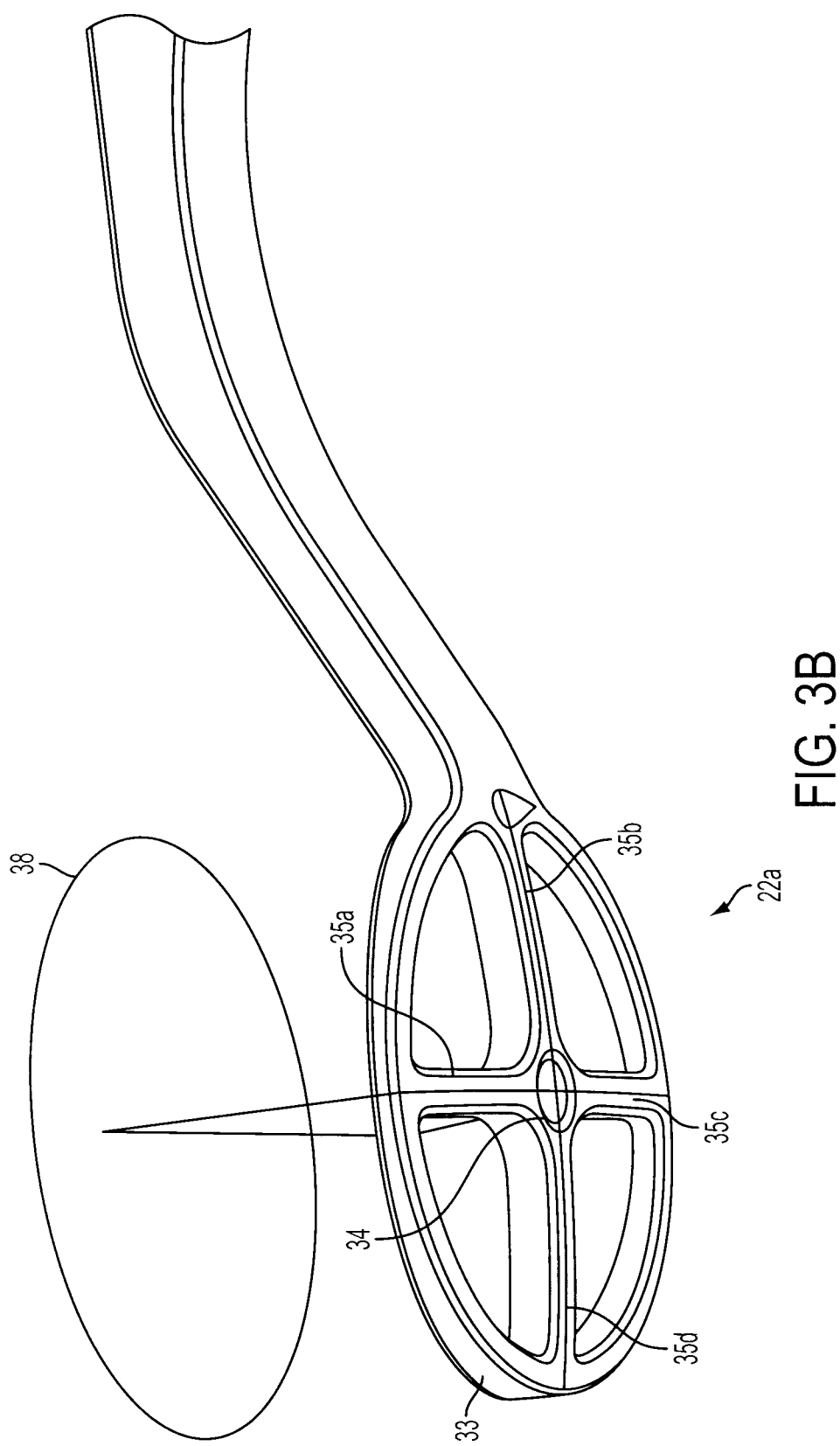
FIG. 3b is a detailed view of another embodiment of an aiming tip consistent with the present disclosure.

Another embodiment of an aiming tip 22a is shown in FIG. 3b. Similar to the above described embodiment, the aiming tip 22a may include a generally centrally located opening 34, and the aiming tip 22a may have a projected area that may generally correspond to the projected geometry of a load bearing surface of an articular surface implant. The aiming tip 22a may include a rim 33 and spokes 35a-d that may define the contact geometry of the aiming tip 22a. That is, rather than having a generally continuous surface, the contacting surface of the aiming tip 22a may include rim 33 and spokes 35a-d. In the illustrated embodiment, the rim 33 may provide a circumferential contacting surface and the spokes 35a-d may provide two generally orthogonal lines of contact. The rim 33 and spokes 35a-d may together define the contact geometry of the aiming tip 22a.

In the illustrate embodiment four spokes 35a-d are provided to define two generally orthogonal contact lines or geometry curves of the aiming tip 22a. In other embodiments consistent with the present disclosure, a greater or fewer number of spokes may be used to define the contact geometry of the aiming tip 22a. Similarly, the spokes 35a-d may be arranged to provide a relationship other than orthogonal. For example, a more complex contact geometry may be defined by five or more spokes. Furthermore, the aiming tip 22a may be provided having a non-circular projected area 38, including for example, oval and/or asymmetrical projected areas.

As with the previous embodiment, the aiming tip 22a may be used in the manner of a feeler gauge, or trial gauge, to determine the desired size and geometry of an implant to replace a portion of an articular surface. As described, the size of the implant may be ascertained based on the projected area 38 of the aiming tip 22a. The rim 33 and spokes 35a-d defining the contacting geometry of the aiming tip 22a may be used to ascertain the geometry of the articular surface based on the degree of fit between the aiming tip 22a and the articular surface. A plurality of aiming tips 22a having different projected areas 38 and/or contact geometries, as defined by the rim 33 and spokes 35a-d, may be positioned on the articular surface in the region of the articular surface to be replaced, and the size and fit between the aiming tip 22a and the articular surface may be ascertained visually, tactilely, and/or using various imaging techniques.

The open structure of the aiming tip 22a, including a rim 33 and spoke 35a-d structure, may allow improved visibility during and after positioning of the aiming tip 22a relative to the articular surface. The improved visibility may permit more controlled placement of the aiming tip 22a on the articular surface. The improved visibility may also allow the fit between the aiming tip 22a and the articular surface to be more easily ascertained. For example, it may be possible to visually determine the fit between one or more of the spokes 35a-d about at least a portion of the length of the spoke. Additionally, the open structure of the aiming tip 22a may be lighter and more easily manipulated. The open structure may also facilitate the passage of tools, fluids, etc. through the aiming tip 22a. Various other features and advantages of the aiming tip 22a will be readily appreciated by those having skill in the art.

Figure 4:
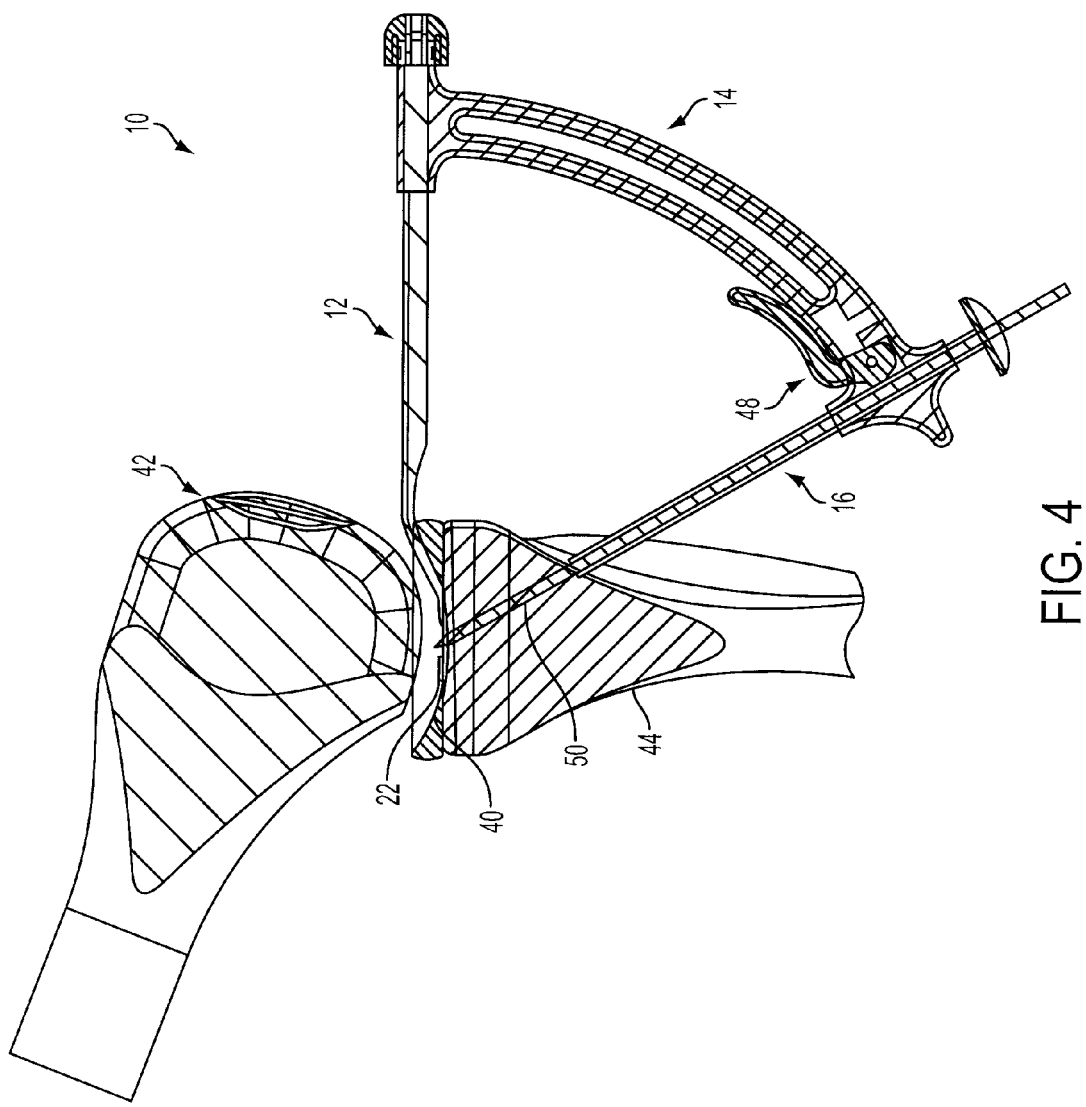
FIG. 4 is a cross-sectional view of a drill guide consistent with the present disclosure in an application for providing retrograde access to an articular surface.

Turning to FIG. 4, an embodiment of the drill guide system 10 is shown in use. The aiming tip 22 is shown positioned within an articular joint and between two cooperating articular surfaces 40, 42. As described above, the aiming tip 22 may be positioned on one of the articular surfaces 40 and generally centered around and/or locating a defect or other portion of the articular surface. With the aiming tip 22 positioned in a location relative to the articular surface 40, the drill guide system 10 may be stabilized relative to the articular surface 40. As shown the cannulated shaft 16 may be advanced to contact a portion of the bone 44 at a location behind the articular surface 40. As best illustrated in FIG. 1 the cannulated shaft 16 may include a serrated distal end 46. The serrated distal end 46 of the cannulated 16 may reduce and/or eliminate movement and/or sliding of the cannulated shaft 16 on the bone 44. The engagement between the serrated distal end 46 and the bone 44 may provide a more secure and/or stabile position of the drill guide system 10 relative to the articular surface 40. The frame 14 may include a locking feature 48, e.g. a cam, ratchet, frictional lock, etc. The locking feature 48 may maintain the cannulated shaft 16 in engagement with the bone 44.

Retrograde access to the articular surface 40 may be initiated by inserting a guide pin 50 through the bone 44 and toward the articular surface. The guide pin 50 may be configured as a self-drilling pin. For example, the guide pin 50 may include drill features on at least a portion of the distal end of the guide pin 50. The lumen of the cannulated shaft 16 and the aiming member 12 may be maintained in a positional and/or angular relationship to one another by the frame 14. In one embodiment, the relationship of the cannulated shaft 16 and the aiming member 12 may be such that the lumen of the cannulated shaft 16 intersects with the opening 34 defined in the aiming tip 22. Accordingly, the guide pin 50 may be positioned extending through the lumen of the cannulated shaft 16. The cannulated shaft 16 may stabilize the guide pin 50 and maintain the guide pin 50 in a desired orientation. The guide pin 50, stabilized by the cannulated shaft 16, may be drilled into the bone 44, for example by hand, or using a drive motor. The guide pin 50 may be drilled into the bone 44 until the distal end of the guide pin 50 penetrated the articular surface 40. According to one embodiment, penetration of the guide pin 50 through the articular surface 40 may be observed through the opening 34 through the aiming tip 22 of the aiming member 12. In one such embodiment, the guide pin 50 may intersect the opening 34 through the aiming tip 22. The guide pin 50 drilled into the bone 44 to the articular surface 40 in this manner may establish a reference axis for subsequent procedures.

Once a reference axis through the bone 40 to the desired location on the articular surface 40 has been established by the guide pin 50, retrograde access to the articular surface 40 may be established to enable subsequent retrograde procedures. After the guide pin 50 has been positioned extending through the bone 44, the drill guide system 10 may be removed. The guide pin 50 may remain extending through the bone 44 establishing the reference axis after the drill guide system has been removed.

Figure 5:
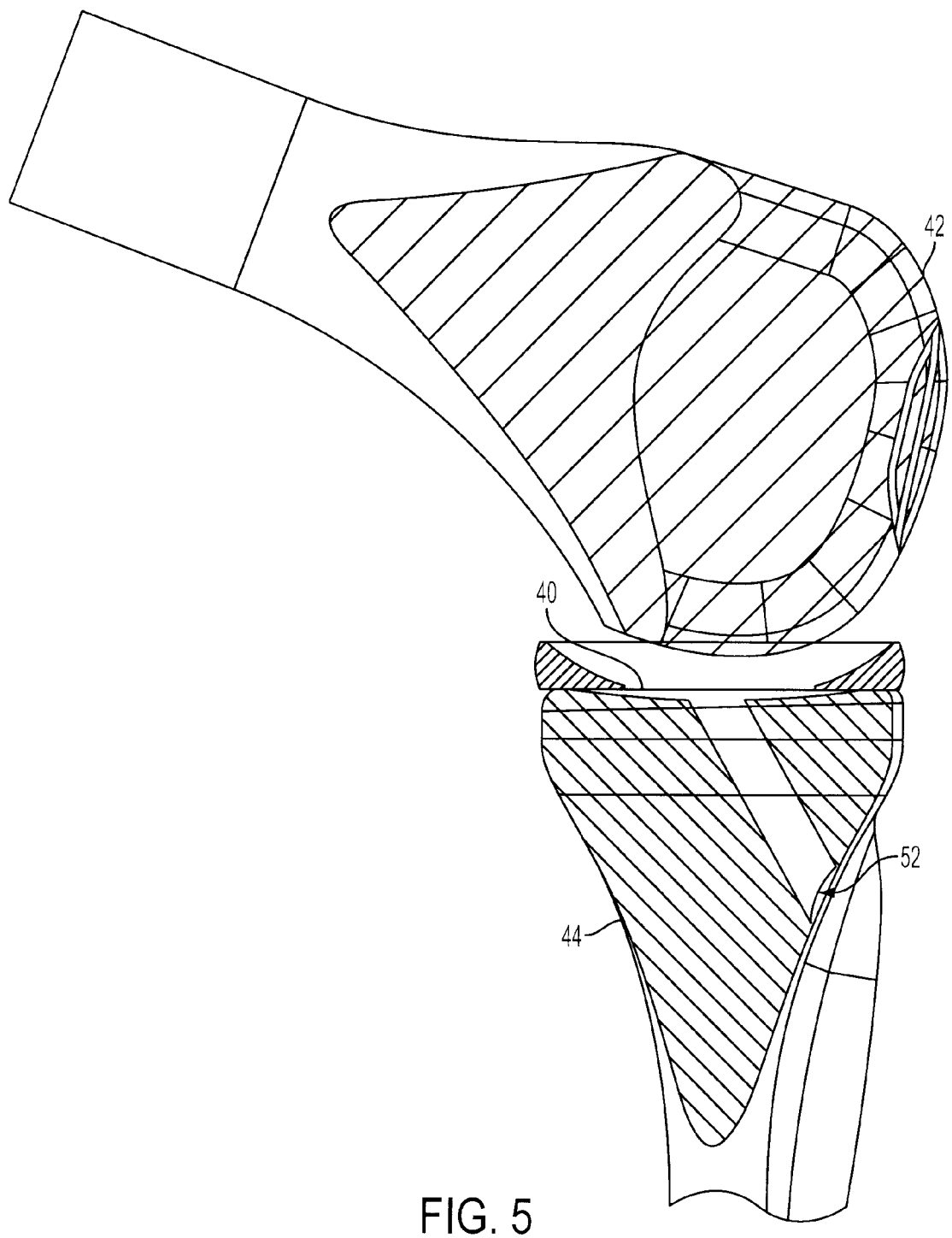
FIG. 5 illustrates an articular joint in cross-sectional view including a retrograde access tunnel.

Referring to FIG. 5, a retrograde access tunnel 52 may be created along the reference axis extending though the bone 44 and to the articular surface 40. According to one embodiment, the access tunnel 52 may be created using a cannulated drill, such as a cannulated twist drill. The cannulated drill may be threaded over the guide pin 50, with the guide pin 50 supporting the cannulated drill and aligning the drill along the reference axis. The access tunnel 52 may then be drilled through the bone 44, operating the cannulated drill either manually or by using a drive motor. The cannulated drill may be carried by the guide pin 50 extending through the lumen of the cannulated drill. The access tunnel 52 may, accordingly, be created along the reference axis. The depth of the access tunnel 52 may be controlled by visual observation. For example, the articular surface 40 may be arthroscopically monitored. Drilling of the access tunnel 52 may be carried out until the cannulated drill penetrates through the articular surface 40 by a generally desired amount. Alternatively, the depth of the access tunnel 52 may be controlled according to another methodology, for example, based on markings or features on the guide pin 50.

Figure 6:
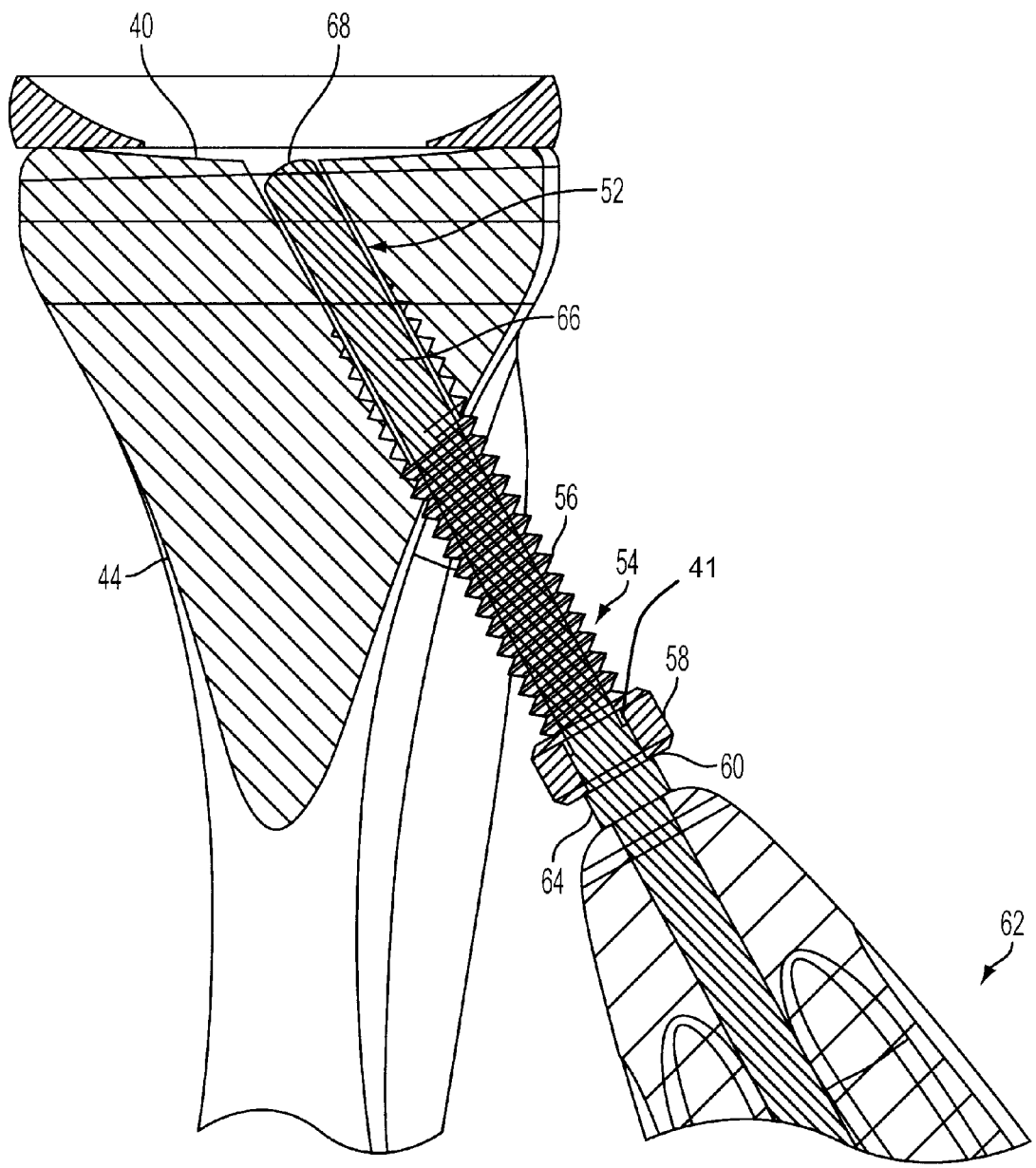
FIG. 6 illustrates a screw sheath inserted into a retrograde access tunnel.

Turning to FIG. 6, after a retrograde access tunnel 52 has been created extending through the bone 44 along the reference axis, a sheath 54 may be at least partially inserted into the access tunnel 52. The sheath 54 may reinforce the access tunnel 52 to prevent damage to the bone 44 through which the access tunnel 52 is defined. The sheath 54 may also provide a bushing or bearing surface for subsequent procedures, and/or the sheath 54 may provide and/or ensure positive alignment with the reference axis.

In one embodiment, the sheath 54 may be provided as a screw sheath. As shown in FIG. 6, a screw sheath 54 may be generally configured having a tubular body 56 and a head 58. The tubular body 56 may be threaded on at least a portion of the outside diameter thereof. The head 58 of the screw sheath 54 may have an outside diameter greater than the outside diameter of the tubular body 56 of the sheath 54. While the illustrated embodiment of the sheath is shown including a head having a larger outside diameter than the body, this is not a necessary feature. Consistent with various alternative embodiments, the head may have an outside diameter that is the same as, or smaller than, the outside diameter of the body. According to still further embodiments, the sheath may not include head. In such an embodiment, the tubular body may make up the entire sheath, with at least a portion of the outside diameter of the tubular body being threaded.

The sheath 54 may be screwed into the access tunnel 52 in the bone 44. Screwing the sheath 54 into the access tunnel 52 may include at least partially threadably engaging the tubular body 56 of the sheath 54 with the inside diameter of the access tunnel 52. The outside diameter of the sheath 54 and the depth of the threaded portion of the body 56 and the inside diameter of the access tunnel 52 may be selected to provided threaded engagement between the sheath 54 and the access tunnel 52. The coordination of the diameters of the sheath 54 and the access tunnel 52 may also be coordinated to minimize excessive and/or undesired damage to the bone 44 when the sheath is screwed into the access tunnel 52. Additionally, the diameters of the sheath 54 and the access tunnel 52 and the pitch, etc., of the threaded portion of the tubular body 56 may be selected to facilitate and/or promote alignment of the sheath 54 with the axis of the access tunnel 52 when the sheath 54 is screwed into the access tunnel 52. Initial alignment of the sheath 54 with the access tunnel 52 may be facilitated by providing the distal end of the sheath, and/or the outer opening of the access tunnel 52, having a chamfer or taper.

The sheath 54 may be screwed into the access tunnel 52 by rotationally driving the sheath 54 in order to engage the threaded portion of the tubular body 56 with the access tunnel 52 and to threadably advance the sheath 54 into the access tunnel 52. As shown, the head 58 of the sheath 54 may include a socket 60 defined therein. According to one embodiment, the socket 60 may be a hex, spline, etc. socket. The sheath 54 may be driven into the access tunnel 52 using a driver 62 including drive head 64 that is shaped to be received in the socket 62 in a torsionally rigid manner, thereby allowing torque to be transmitted from the driver 62 to the sheath 54.

The driver 64 may include a shaft 66 sized to extend through the tubular body 56 of the sheath 54. The shaft 66 may be provided as an extension of the drive head 64, or may be a separate component extending through the drive head 64 and into the tubular body 56 of the sheath 54. The shaft 66 may be employed to position a distal end of the sheath 54 in the bone 44 at a depth below the articular surface 40. Depth positioning of the sheath 54 relative to the articular surface 40 may be accomplished by providing the shaft 66 having a known length relative to the length of the sheath 54. According to one embodiment, a shoulder 41 may be defined by the bottom of the socket 60 and the cannula through the tubular body 56 of the sheath 54. The shoulder may allow the drive head 64 to positively seat in the socket 60. Accordingly, when the drive head 64 is seated in the socket 60 the extension of the shaft 66 beyond the distal end of the sheath 54 may be ascertained by direct measurement and/or by calculation based on the respective length of the shaft 66 and of the sheath 54.

In another embodiment, the drive head 64 of the driver 62 may include a shoulder having a larger diameter than the socket 60. Accordingly, when the drive head 64 is engaged in the socket 60 the shoulder of the drive head 64 may bear against the head 58 of the sheath 54. Accordingly, the projection of the shaft 66 beyond the distal end of the sheath may be the difference between the length of the shaft 66 from the shoulder of the drive head 64 and the length of the sheath 54. Of course, the projection of the shaft 66 beyond the distal end of the sheath 54 may also be directly measured. This embodiment may be used alone, in combination with the preceding embodiment, and/or in combination with any of various other arrangements that may be used to provide a repeatable and/or relatively stable extension of the shaft 66 beyond the distal end of the sheath 54.

According to any of the preceding embodiments, the distal end of the sheath 54 may be positioned at a depth below the articular surface 40 by driving the sheath 54 into the access tunnel 52, and thereby threadably advancing the sheath 54 within the access tunnel 52, until the distal end 68 of the shaft 66 reaches a predetermined height relative to the articular surface 40. According to an embodiment consistent with the present disclosure, the projection of the shaft 66 beyond the distal end of the sheath 54 may be equal to the desired final depth of the distal end of the sheath below the articular surface 40. Accordingly, the sheath 54 may be threadably driven into the access tunnel 52 until the distal end 68 of the shaft 66 is tangent, or flush, with the articular surface 40. According to various other embodiments, the relative extension of the shaft 66 beyond the distal end of the sheath 54 may be such that the distal end of the sheath 54 is at the desired depth below the articular surface 40 when the distal end 68 of the shaft 66 is either recessed below the articular surface 40 or when the distal end 68 of the shaft 66 protrudes above the articular surface 40. The necessary amount of recess below, or protrusion above, the articular surface 40 may be ascertained by measuring or by reference to indicia on the shaft 66, etc.

Figure 7:
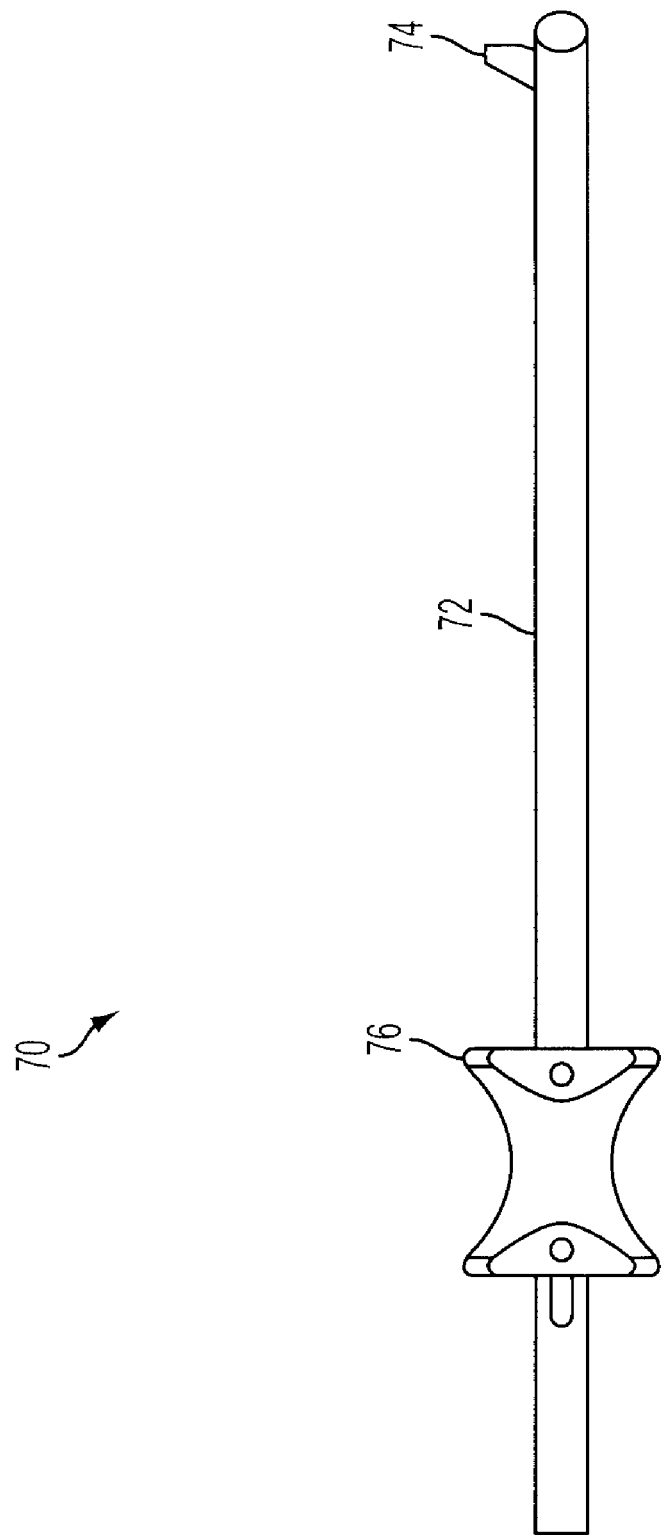
FIG. 7 shows an embodiment of an excision device consistent with the present disclosure in plan view.

According to one embodiment, the sheath 54, positioned within the access tunnel 52 with the distal end of the sheath 54 located a predetermined distance below the articular surface 40, may be used to support an excision device 70 to enable at least a portion of the articular surface 40 to be excised. Turning to FIG. 7, an embodiment of an excision device 70 that may be used for excising at least a portion of the articular surface 40 is shown. Generally, the excision device 70 may include a drive shaft 72 that is sized to be received through the tubular body 56 of the sheath 54. In one embodiment, the excision device 70 may also include a cutter 74 adjacent the distal end of the shaft 72 and a handle 76 disposed adjacent the proximal end of the shaft 72.

Figure 8:
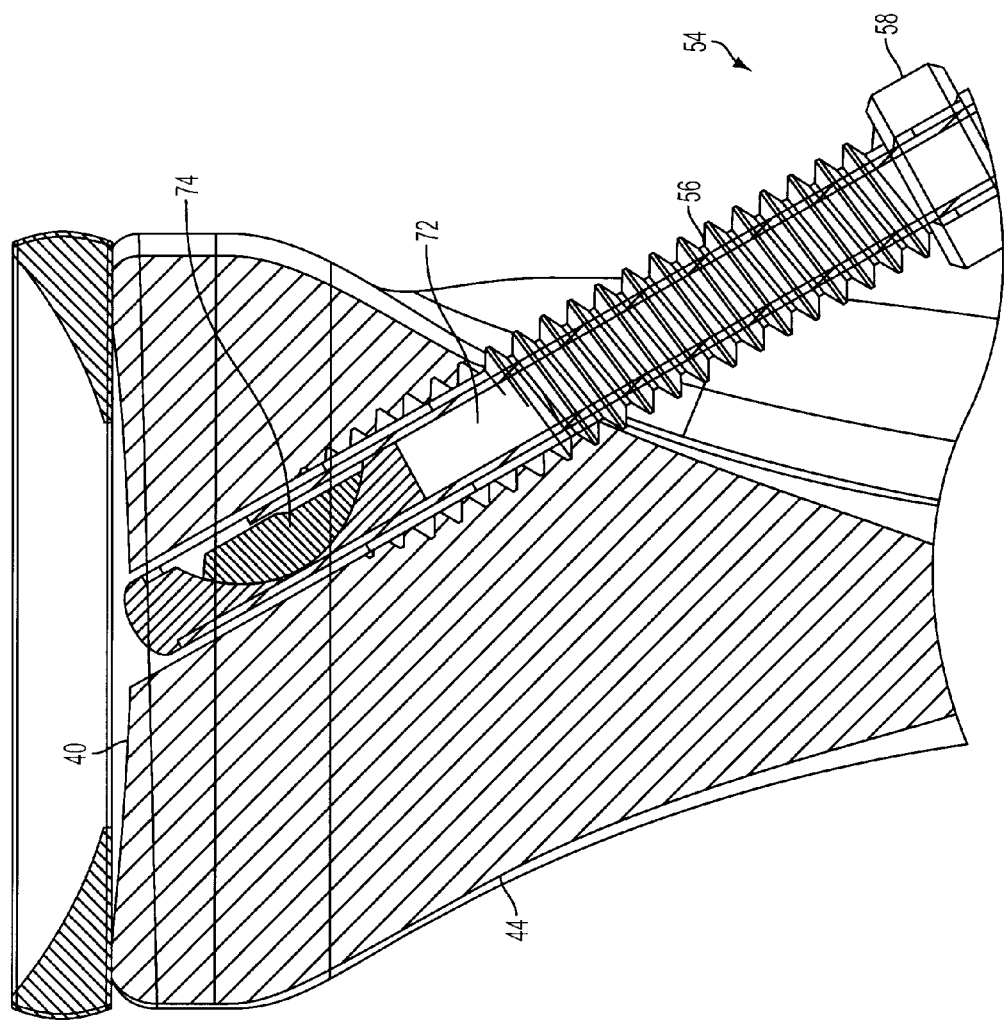
FIG. 8 illustrates, in cross-sectional view, an embodiment of an excision device consistent with the present disclosure.

Referring to FIG. 8, the distal end of the excision device 70 is shown received through the sheath 54. As depicted, the cutter 74 may be placed in one position, for example, such that the cutter 74 is configured to be at least partially retracted to allow the distal end of the shaft to be inserted into and/or through the sheath 54. While the cutter 74 is shown retracted entirely within the diameter of the shaft 72, other embodiments are contemplated by this disclosure. Consistent with the illustrated embodiment, the outside diameter of the shaft 72 of the excision device 70 may be sized to be rotatably and/or slidable received within the inside diameter of the sheath 54. According to one embodiment, the tolerance between the outside diameter of the shaft 72 of the excision device 70 and the inside diameter of the sheath 54 may be such that, while the shaft may be rotatably and/or slidably disposed within the sheath 54, the shaft 72 of the excision device 70 may be maintained generally aligned with the axis of the sheath 54.

Figure 9:
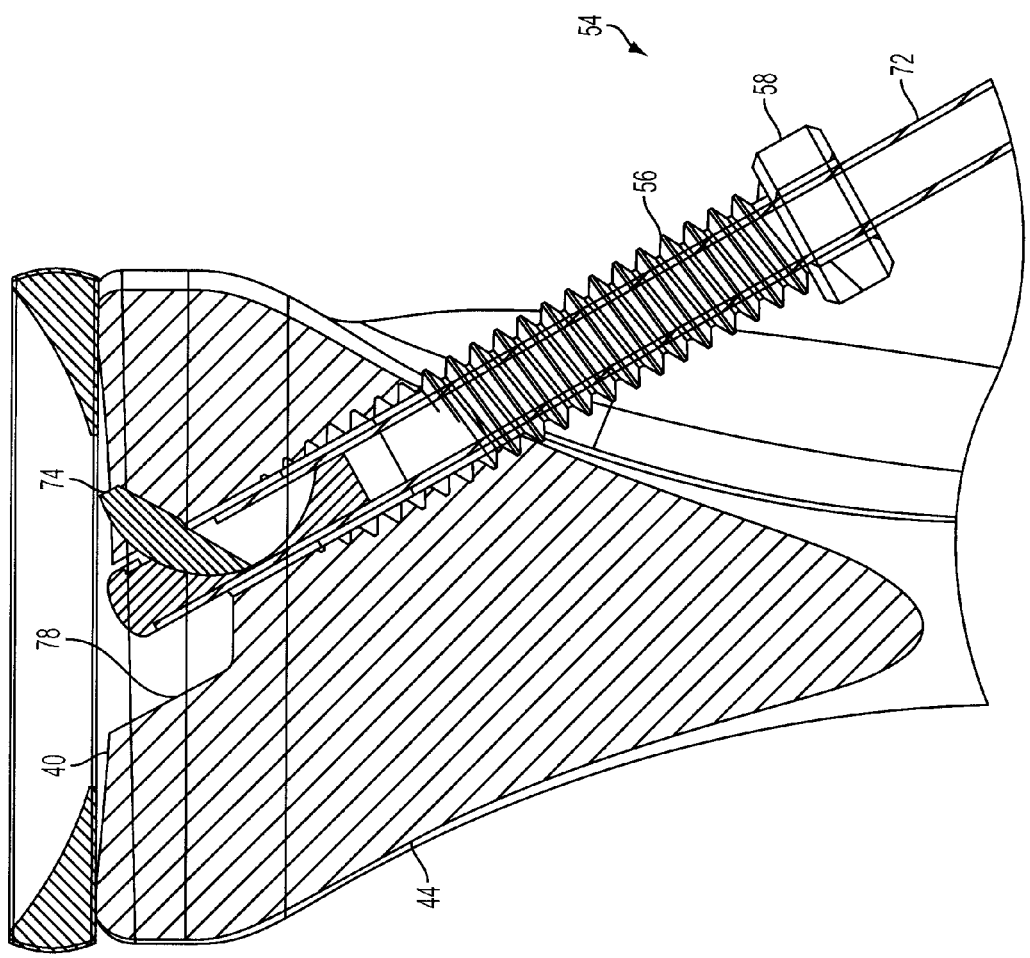
FIG. 9 illustrates the excision device depicted in FIG. 8 with a cutter of the excision device in a deployed configuration.

Turning next to FIG. 9, the cutter 74 may be moved to another position, for example a deployed configuration, in which the cutter 74 extends outwardly from the shaft 72. Excision of the articular surface 40 and/or excision of the underlying bone 44 may be achieved by rotating the excision device 70 during and/or after deployment of the cutter 74. According to one embodiment, the excision device 70 may be positioned so that at least a portion of the cutter 74 is disposed below the articular surface 40. The cutter 74, and the shaft 72 therewith, may be rotated as the cutter 74 is deployed, thereby excising an implant site 78 in the articular surface 40 and/or the underlying bone 44. The cutter 74 may be configured to be gradually and/or incrementally moved to the deployed configuration. Accordingly, the articular surface 40 and/or bone 44 may be gradually excised. While not necessary, gradual excision may, in some situations, decrease the occurrence of irregular and/or undesired chipping, cracking, fragmenting, etc., of the bone 44 and/or of the articular surface 40.

According to another embodiment, the excision device 70 may be advanced into the joint so that at least a portion of the cutter 74 is disposed above the articular surface 40. The cutter 74 may then be at least partially deployed, with at least a portion of the cutter 74 being deployed above the articular surface 40. The cutter 74, and the shaft 72 therewith, may be rotated before, during, and/or after the at least partial deployment of the cutter 74. As the cutter 74 and shaft 72 are rotated the excision device 70 may be withdrawn, thereby urging the cutter 74 into the articular surface 40. Various other methodologies my also be employed to excise an implant site 78 in the articular surface 40 and/or in the underlying bone 44 using an excision device 70 according to the present disclosure.

Consistent with the illustrated embodiment, the configuration of the distal tip of the excision device 70 and the mode of deployment of the cutter 74 may be such that collateral damage to adjacent bone and/or articular cartilage, for example of an adjacent cooperating articular surface e.g. 42 in FIG. 5, may be reduced and/or prevented. Additionally, as most clearly observed in FIG. 11, the cutter 74 may include a shelf 75 that may contact and/or bear against a distal end of the sheath 54 as cutter 74 is withdrawn towards the sheath 54 during the excision of the articular surface 40 and underlying bone 44. The interaction of the shelf 75 and the distal end of the sheath 54 may, with the distal end of the sheath 54 located a predetermined distance below the articular surface 40, control the depth of the implant site 78 created by excising the articular surface 40 and the underlying bone 44. The shelf 75 of the cutter 74 may have a flat, relieved, and/or rounded profile to reduce and/or eliminate grinding, shaving, or otherwise freeing fragments of the sheath 54 when the cutter 74 contacts the distal end of the sheath 54.

Figure 10:
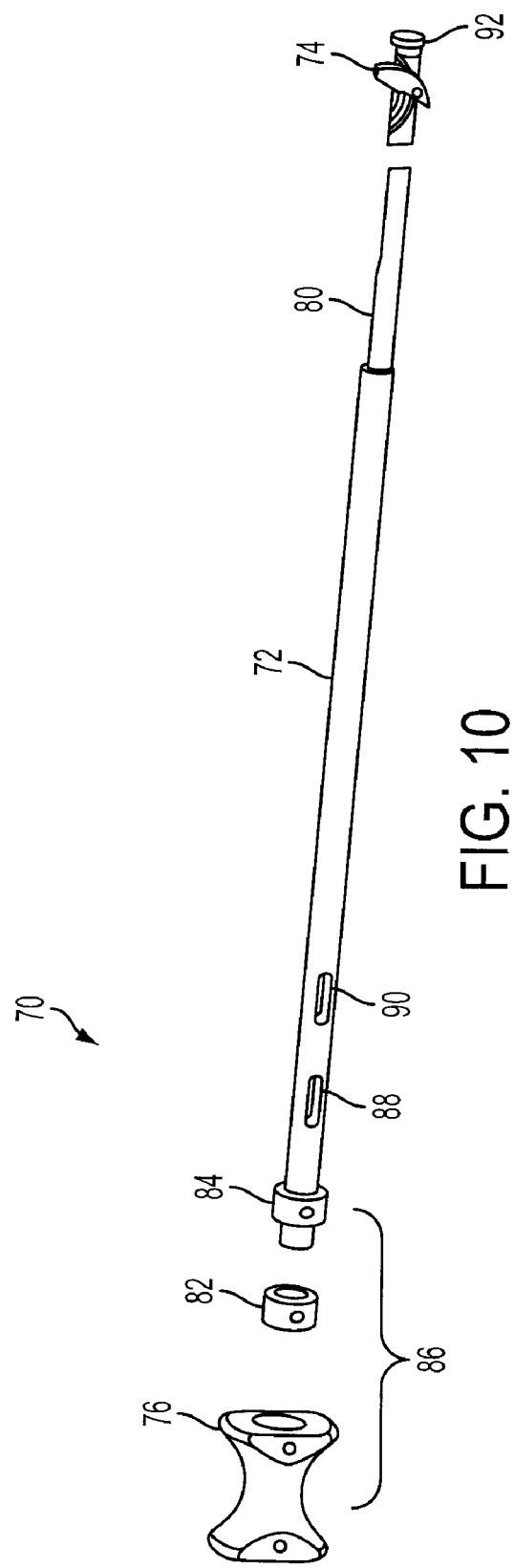
FIG. 10 is an exploded view of an excision device consistent with the present disclosure.

Referring to FIG. 10, an exploded diagram of an embodiment of an excision device 70 consistent with the present disclosure is shown. In addition to the shaft 72, the cutter 74, and the handle 76, the excision device 70 may also include a pushrod 80 extending generally between the cutter 74 and the handle 76. One or more bearings 82, 84 may be associated with the handle 76 to provide a hub assembly 86. The shaft 72 of the excision device 70 may be rotatably received at least partially within the hub assembly 86 provided by the handle 76 and bearings 82, 84. The shaft 72 may further include one or more longitudinal slots 88, 90 in the general region of the hub assembly 86. The longitudinal slots 88, 90 may allow the pushrod 80 to be axially translated within the shaft 72. The distal end of the excision device 70 may include a cutter tip 92 that may carry the cutter 74.

Turning next to FIG. 11, the distal end of the excision device 70 is shown in a detailed exploded view. As illustrated, the distal end of the shaft 72 may include a cutter deployment window 94 though which the cutter 74 may extend or project when the cutter 74 is in a deployed configuration. The cutter tip 92 may be sized to be at least partially received inside the cannulated shaft 72. The cutter tip 92 may be retained in the shaft 72 using any suitable means or configuration, including friction fit, adhesive bonding, welding, staking, etc.

Consistent with the illustrated embodiment, the excision device 70 may employ a system of arcs-in-grooves to enable the cutter 74 to move between a stowed, or retracted, configuration and a deployed, or extended, configuration. The arcs-in-grooves arrangement may create a virtual pivot about which the cutter 74 may pivot or rotate between the stowed configuration and the deployed configuration. Consistent with the present disclosure, the virtual pivot is a point or an axis about which the cutter 74 may rotate. However, the cutter 74 is not physically connected to the virtual pivot, e.g., as by an axle or pivot pin. As such, the cutter 74 may be capable of being engaged to the drive shaft 72, for example, through the system of arcs-in-grooves.

The arcs-in-grooves arrangement utilized herein may provide relative simplicity from the stand-point of mechanical operation and assembly. Additionally, the arcs-in-grooves arrangement may provide a moment arm between the cutter 74 and the virtual pivot point that is greater than the moment arm that may be achieved by rotating the cutter 74 around an actual physical pivot, such as a pin, within the same package size, i.e., within the diameter of the shaft 72. The longer moment arm achievable using a virtual pivot in an arcs-in-grooves arrangement may allow the cutter 74 to achieve a relatively higher deployment torque for a given actuation force.

The cutter tip 92 may include a primary arcuate groove 96 and a secondary arcuate groove 98. As shown, the primary and secondary grooves 96, 98 may be provided as concave surfaces extending into the cutter tip 92. The primary and the secondary arcuate grooves 96, 98 may be concentric with one another. Additionally, each of the primary and the secondary arcuate groove 96, 98 may have a constant radius. Consistent with the illustrated embodiment, while the primary and secondary arcuate grooves 96, 98 may be concentric and may each have a constant radius, the radius of one of the arcuate grooves, e.g. the primary arcuate groove, may be greater than the radius of the other arcuate groove, e.g., the secondary arcuate groove 98.

The cutter 74 may include a primary arcuate bearing surface 100 and a secondary arcuate bearing surface 102. Similar to the primary and the second arcuate grooves 96, 98, the primary and secondary arcuate bearing surfaces 100, 102 may each have a constant radius and may be concentric with one another. Additionally, in one embodiment the primary and secondary arcuate bearing surfaces 100, 102 of the cutter 74 may be provided as the compliment of the primary and the secondary arcuate grooves 96, 98. That is, the primary and secondary arcuate bearing surfaces 100, 102 may cooperate with the primary and the secondary arcuate grooves 96, 98 to allow arcuate sliding movement of the cutter 74 about the center of the primary and the secondary arcuate grooves 96, 98. The foregoing interaction between the primary and secondary arcuate grooves 96, 98 and the primary and secondary arcuate bearing surfaces 100, 102 does not require that the radii of the primary and secondary arcuate bearing surfaces 100, 102 be the same as the respective radii of the primary and the secondary arcuate grooves 96, 98.

According to a related embodiment, the cutter may include an arcuate protrusion in addition to and/or instead of the primary and secondary arcuate bearing surfaces. The arcuate protrusion or rib may be received in a channel in the tip, the channel having an arcuate cooperating feature corresponding to the arcuate protrusion. According to such an arrangement, cutter may rotate about a virtual pivot as discussed above. The interaction of the protrusion and the channel may restrict and/or limit non-rotational movement of the cutter, e.g. wobbling, twisting, or translation of the cutter along the pivot axis. The protrusion and channel configuration may therefore, in some embodiments, further stabilize the cutter. In a similar embodiment, the cutter tip may be provided having an arcuate protrusion that may be received in a channel in the cutter. The operation of such an embodiment may be as generally described.

Figure 12:
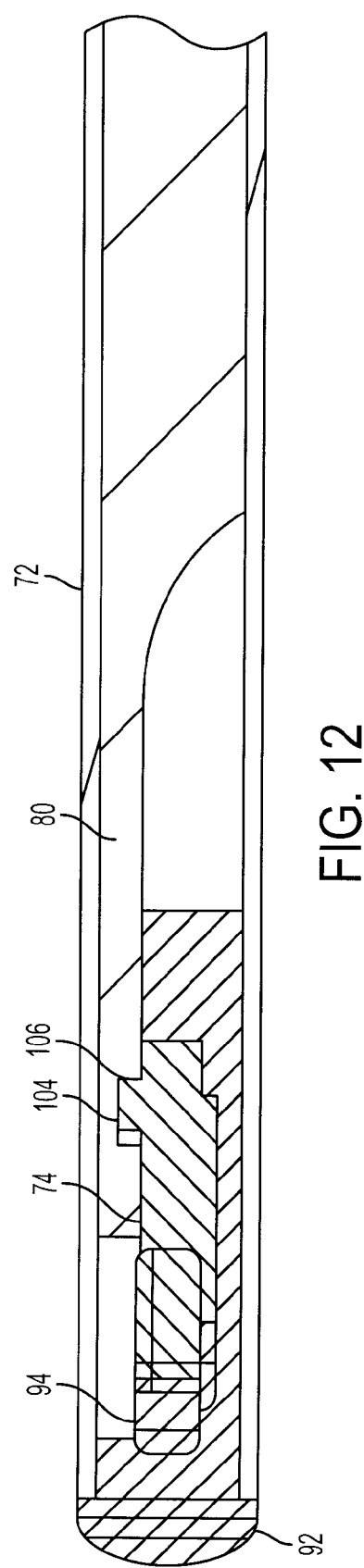
FIG. 12 is cross-sectional view of a distal end of an excision device consistent with the present disclosure.

With additional reference to FIG. 12, in the illustrated excision device 70, actuation of the cutter 74 may be achieved using the pushrod 80 slidably disposed within the shaft 72, which may, in some embodiments be a cannulated shaft. The cutter 74 may include a boss 104 that may be at least partially received within a slot 106 of the pushrod 80. Translating the pushrod 80 axially toward the distal end of the excision device 70 may urge the cutter 74 toward the distal end of the excision device 70. Cooperation of the primary and secondary arcuate bearing surfaces 100, 102 against the respective primary and secondary arcuate grooves 96, 98 may cause the cutter 74 to rotate within the primary and secondary arcuate grooves 96, 98 about the center of the primary and secondary arcuate grooves 96, 98. Rotation of the cutter 74 about the center of the primary and secondary arcuate grooves 96, 98 may cause the cutter 74 to deploy through the deployment window 94 and extend outwardly from the shaft 72.

Similarly, when the cutter 74 is in a deployed configuration, the cutter 74 may be retracted to a stowed configuration by axially translating the pushrod 80 toward the proximal end of the excision device 70. When the pushrod 80 is axially translated toward the proximal end of the excision device 70, the proximal edge of the slot 106 in the pushrod 80 may bear against the boss 104 of the cutter 74. The force of the slot 106 on the boss 104 may urge the primary and secondary arcuate bearing surfaces 100, 102 toward the proximal portion of the primary and secondary arcuate grooves 96, 98. The force of the primary and second arcuate bearing surfaces 100, 102 against the primary and secondary arcuate grooves 96, 98 may cause the cutter 74 to rotate about the center of the primary and secondary arcuate grooves 96, 98. Rotation of the cutter 74 about the center of the primary and secondary arcuate grooves 96, 98 may cause the cutter 74 to rotate in through the deployment window 94 to achieve a stowed configuration at least partially within the shaft 72.

Figure 13:
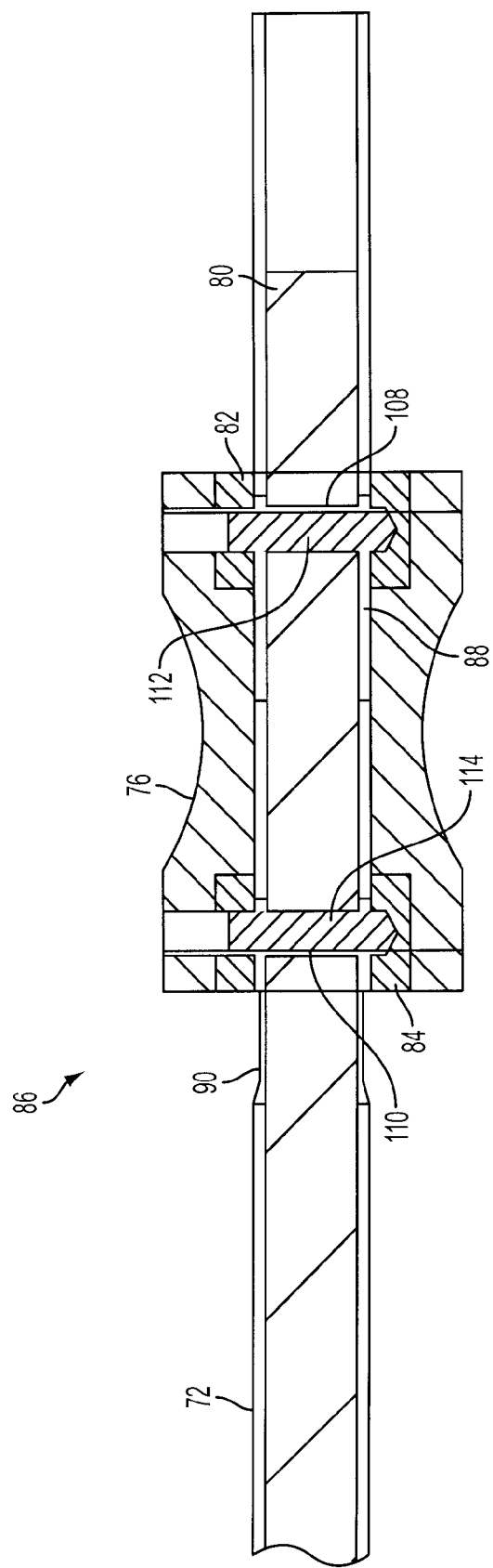
FIG. 13 is a cross-sectional view of a handle region of an excision device consistent with the present disclosure.
Figure 14:
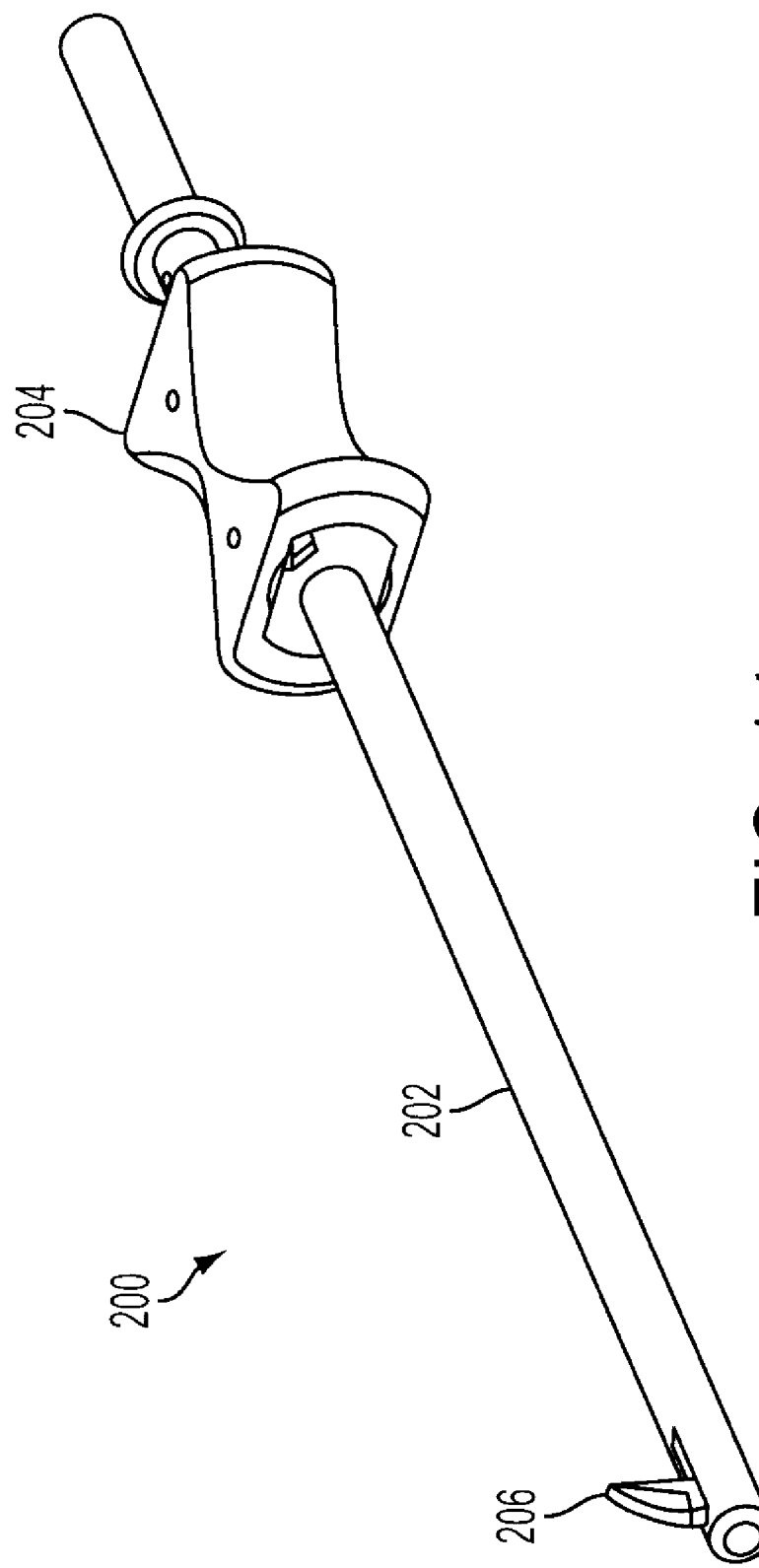
FIG. 14 is a perspective view of another embodiment of an excision device consistent with the present disclosure.

FIG. 13 illustrates an embodiment of the hub assembly 86 in detailed cross-sectional view. Generally, the hub assembly 86 may allow the handle 76 to be maintained rotationally stable or unmoving while the shaft 72, the pushrod 80, and the cutter 74 therewith, may be rotated to excise the articular surface 40 and underlying bone 44. Additionally, the hub assembly 86 may allow the pushrod 80 to be axially translated within the shaft 72 while the shaft 72, along with the pushrod 80, rotate.

Consistent with the illustrated embodiment, the handle 76 may be coupled to the shaft 72 by one or more bearings 82, 84. The bearings 82, 84 may allow the shaft 72 to rotate independently of the handle 76. In addition to allowing the shaft 72 to rotate independently of the handle 76, the bearings 82, 84 may also allow the handle 76 to slide axially along the shaft 72. Axial movement of the handle 76 along the shaft 72 may be achieved as a function of the design and/or construction of the bearings 82, 84. For example, the bearings 82, 84 may facilitate axial as well as rotational movement, e.g., as may be achieved with ball bearings. According to another embodiment, axial movement of the handle 76 relative to the shaft 72 may be a function of the fit between the bearings 82, 84 and the shaft 72. For example, a loose fit between the bearings 82, 84 and the shaft 72 may allow sliding movement of the handle 76 along the shaft 72. Consistent with the present disclosure, the bearings 82, 84 herein may be provided as ball bearing and/or roller bearings. Alternatively, the bearings 82, 84 may be provided as bushings formed from a low friction material, such as bronze, Teflon™, polyethylene, ultra-high molecular weight polyethylene, etc. Other suitable materials, designs, and/or configurations of the bearings may also be employed consistent with the present disclosure.

Actuation of the pushrod 80 within the shaft 72 while the shaft 72 is rotating may be accomplished by sliding the handle 76 along the shaft 72. In the region of the hub assembly 86 the shaft 72 may include one or more axial slots 88, 90, as best observed in FIG. 10. The pushrod 80 may include at least one radially extending hole 108, 110 corresponding to each slot 88, 90. A pin 112, 114 may be provided extending through each hole 108, 110 in the pushrod 80 and at least partially extending from the respective slot 88, 90 in the shaft 72. Each pin 112, 114 may couple each bearing 82, 84 to the pushrod 80 through the slots 88, 90. Accordingly, axial movement of the bearings 82, 84 along the shaft 72 may move the pins 112, 114 in the slots 88, 90, thereby producing axial movement of pushrod 80.

Consistent with the foregoing illustrated and described excision device 70, axial movement of the bearings 82, 84 along the shaft 72 may axially translate the pushrod 80 within the shaft 72. Accordingly, when the shaft 72 is rotated the pushrod 80 and at least a portion of each bearing 82, 84 may rotate with the shaft 72, while the handle 76 may be maintained rotationally stationary. Axial movement of the handle 76 along the shaft 72 may cause axial movement of the bearings 82, 84 along the shaft 72. The axial movement of the bearings 82, 84 along the shaft 72 may cause axial translation of the pushrod 80 within the shaft 72. The axial translation of the pushrod 80 may actuate the cutter 74, moving the cutter 74 between a stowed configuration and a deployed configuration. Accordingly, the shaft 72, pushrod 80, and cutter 74 may be rotated, e.g., by a drive motor, while the excision device 70 may be stabilized by the handle 76, which may also deploy and retract the cutter 74.

Referring to FIGS. 14 through 21, another embodiment of an excision device 200 consistent with the present disclosure is shown. The illustrated excision device 200 may generally include a shaft 202 having a handle 204 disposed adjacent to a proximal region of the shaft 202. The excision device 200 may further include a cutter 206 that is deployable from a distal region of the shaft 202, as illustrated.

Figure 15:
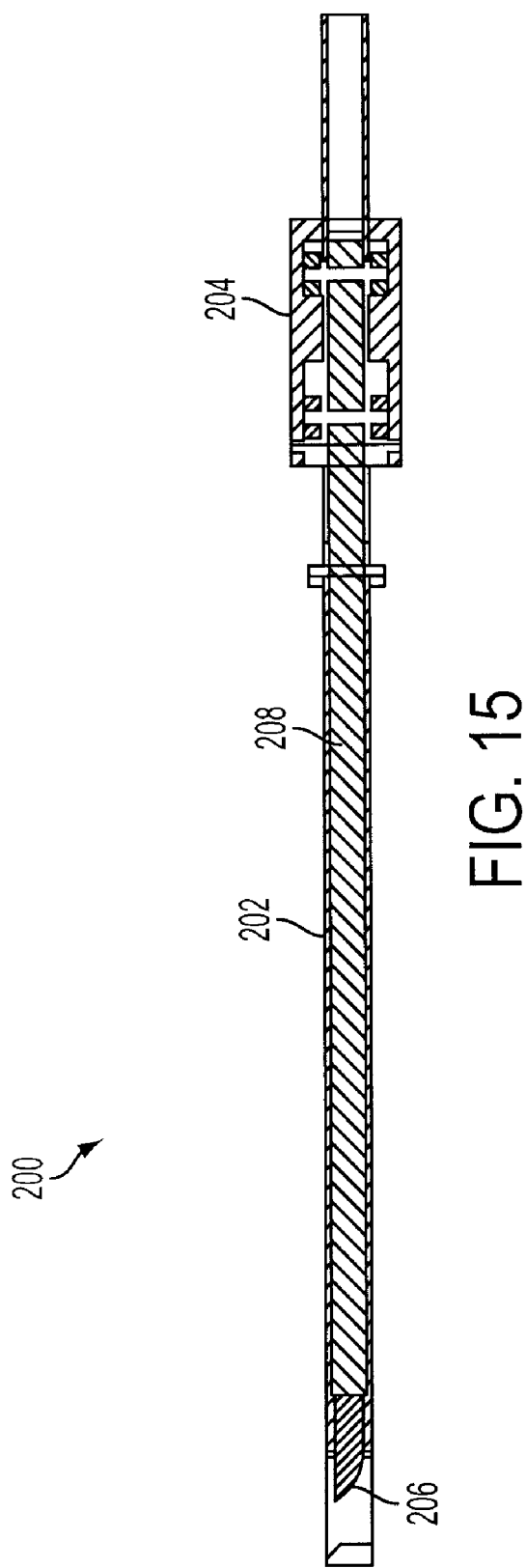
FIG. 15 is a cross-sectional view of the excision device illustrated in FIG. 14 with the cutter in a retracted configuration.

As shown in cross-sectional view in FIG. 15, the shaft 202 of the excision device 200 may be a cannulated shaft. A pushrod 208 may be disposed within the lumen of the cannulated shaft 202. The pushrod 208 may be coupled to the handle 204 at a proximal end, and may be coupled to the cutter 206 at a distal end. The pushrod 208 may be either directly or indirectly coupled to the handle 204 and/or to the cutter 206. When the cutter 206 is in a retracted configuration, as shown in FIG. 15, the cutter 206 may be disposed at least partially and/or completely within the lumen of the cannulated shaft 202.

Figure 16:
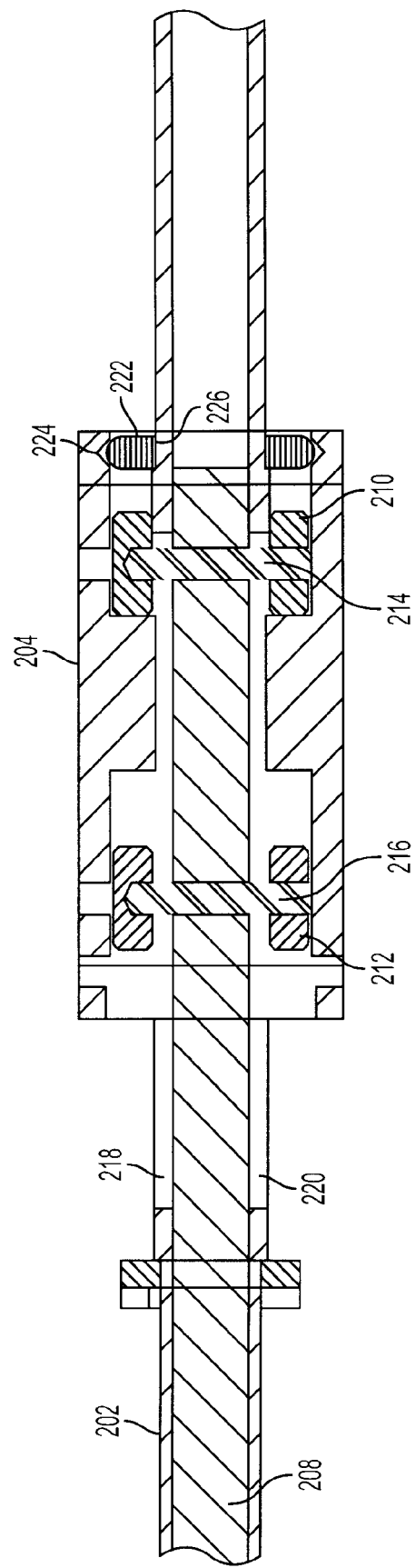
FIG. 16 is a detailed cross-sectional view of the handle region of the excision device depicted in FIG. 14 with the cutter in a retracted configuration.

With reference to FIG. 16, the handle 204 may be slidably and rotatably disposed on the shaft 202. The handle 204 may be coupled to the shaft 202 by two bearings 210, 212. In other embodiments consistent with the present disclosure, a single bearing may suitably be employed for coupling the handle 204 to the shaft 202. The bearings 210, 212 may be ball bearings, roller bearings, bushings, etc. As shown the bearings 210, 212 may be coupled to the pushrod 208 disposed within the lumen of the shaft 202 by pins 214, 216 extending through the pushrod 208 and a pair of opposed slots 218, 220 in the shaft 202. The pins 214, 216 may be received in the bearings 210, 212, thereby coupling the bearings 210, 212 and the pushrod 208.

Consistent with the illustrated embodiment, the shaft 202, pushrod 208 and at least a portion of each bearing 210, 212 may rotate relative to the handle 204. Furthermore, the bearings 210, 212 and the pushrod 208 may be in a generally fixed axial relationship with the handle 204. The handle 204, pushrod 208, and bearings 210, 212 may be slidable disposed on the shaft 202, with the bearings 210, 212 coupled to the pushrod 208 by the pins 214, 216 axially slidably disposed through the slots 218, 220 in the shaft 202.

In one embodiment, the handle 204 may be releasably retained in a proximal position relative to the shaft 202. In the illustrated embodiment, the handle 204 may be releasably retained in a proximal position on the shaft 202 by a ring 222. When the handle 204 is in a proximal position the ring 222 may be at least partially received in a recess 224 in the handle and a recess 226 in the shaft 202. Accordingly the handle 204 may be releasably retained in position on the shaft 202. In one embodiment, at least a portion of the ring 222 may be resiliently radially deflectable. The handle 204 may be released from engagement with the ring 222 by applying a distally directed axial force on the handle 204. The distally directed axial force may cause the ring to compress or deflect radially inwardly from the recess 224 in the handle 204 and allow the handle 204 to move axially from the ring 222. In one embodiment, the handle 204 may be releasably engaged with the ring 222 by applying a proximally directed force on the handle 204, causing the ring 222 to compress or deflect radially inwardly and allowing the recess 224 to move into position and engage the ring 222. As described above, the handle 204 may be in a generally fixed axial relationship relative to the pushrod 208. Accordingly, when the handle 204 is releasably retained in a proximal position on the shaft 202, the pushrod 208 may also be releasably retained in a proximal position relative to the shaft 202.

Figure 17:
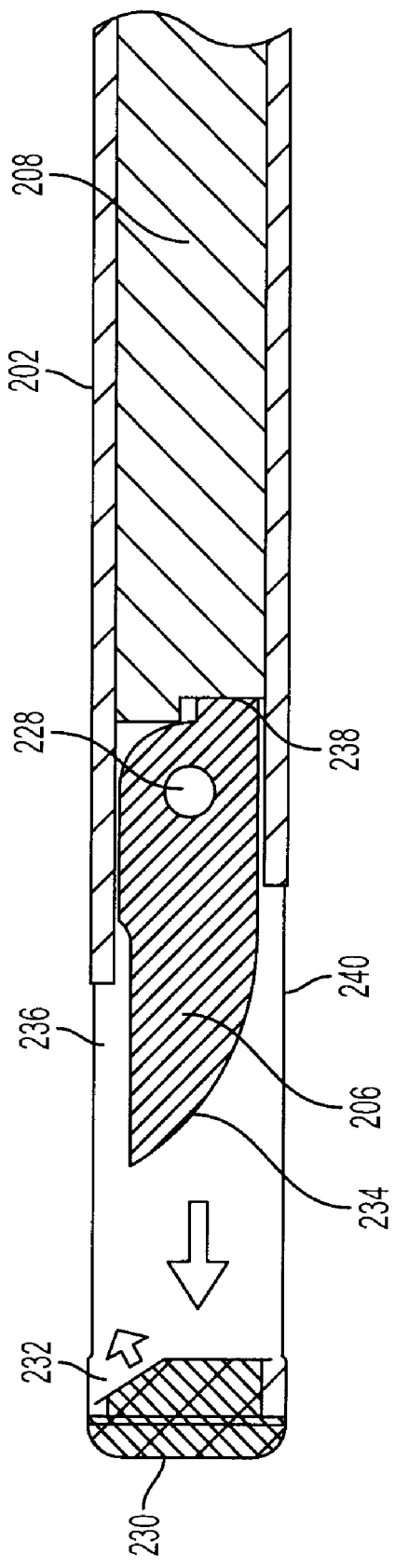
FIG. 17 is a detailed cross-sectional view of the distal end of the excision device of FIG. 14 with the cutter in a retracted configuration.

As shown in FIG. 17, when the handle 204 is in a proximal position, as depicted in FIG. 16, the cutter 206 may be in a retracted or stowed configuration. When the cutter 206 is in a retracted configuration the cutter 206 may be at least partially and/or completely disposed within the lumen of the shaft 208.

The cutter 206 may be pivotally coupled to the pushrod 208 by a pivot pin 228. The pivotal coupling between the cutter 206 and the pushrod 208 may allow the cutter 206 to pivot about an axis generally perpendicular to the axis of the shaft 202. As indicated by the arrows in FIG. 17, moving the cutter 206 distally may urge the cutter 206 against the distal tip 230 of the excision device 200. A portion of the distal tip 230 may include an angled or arcuate surface 232 that may pivot the cutter 206 outwardly when the cutter 206 is urged against the surface 232. A blade portion 234 of the cutter 206 may deploy through a first distal slot 236 in the shaft 202. According to one embodiment, a tab portion 238 of the cutter 206 may be at least partially received in and/or through a second distal slot 240 in the shaft 202.

Figure 18:
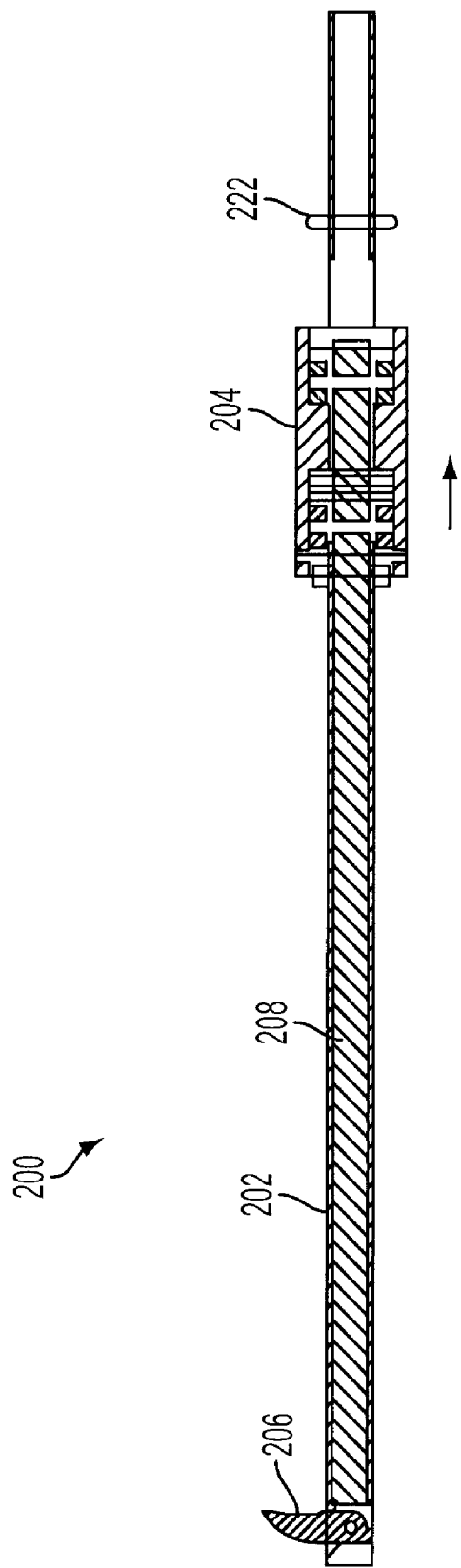
FIG. 18 depicts the excision device of FIG. 14 in cross-sectional view with the cutter in a deployed configuration.
Figure 19:
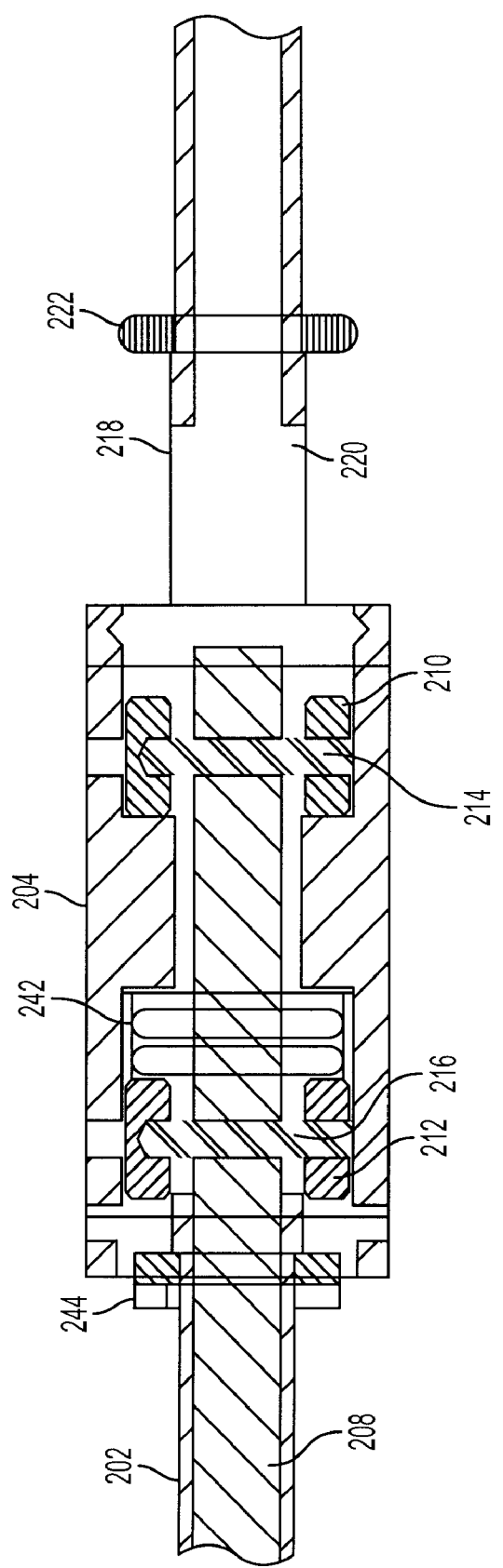
FIG. 19 is a detailed cross-sectional view of the excision device of FIG. 14 with the cutter in a deployed configuration.

With specific reference to FIGS. 18 and 19, the excision device 200 is illustrated with the handle 204 in a distal position. As shown, when the handle 204 is in a distal position, the pushrod 208 is also in a distal position, and the cutter 206 may be in a deployed configuration, extending at least partially from the shaft 202. The handle 204 may be released from the ring 222 in a distal position, thereby allowing sliding and rotational movement of the handle 204 with respect to the shaft 202.

As shown in FIG. 19, when the handle 204 is in a distal position, the pins 214 and 216 may be in a distal position within the slots 218, 220 in the shaft 202. Additionally, in a distal position the handle 204 may contact a resilient feature 242. The resilient feature 242 may be resiliently deflectable or deformable along the axis of the shaft 202. Accordingly, when the handle 204 is move distally against the resilient feature 242, the resilient feature 242 may deflect or deform to permit distal movement of the handle 204, while applying a proximally directed spring force against the handle 204. Consistent with an embodiment herein the resilient feature 242 may be a spring, such as a short coil spring or a wave spring. As used herein, a wave spring may generally resemble a washer having an undulating configuration that is resiliently deflectable. Various other springs and resilient features, e.g., elastically deformable features, may be used herein.

The handle 204 may be urged distally against the spring force of the resilient feature 242 and the handle may engage locking feature 244. The locking feature 244 may engage the handle 204 to maintain the handle 204 in a distal position. According to one embodiment, the locking feature 244 may be a twist-lock feature. In such an embodiment, the handle 204 may be moved distally to engage the locking feature 244 and then the handle may be rotated about the shaft 202 relative to the locking feature 244 thereby releasably engaging the locking feature 244. In one specific embodiment, the locking feature 244 may be partially received in a distal end of the handle 204. When the handle 204 is rotated relative to the locking feature 244 cooperating features, such as protrusions and indentations, on the handle 204 and locking feature 244 may engage one another to releasably retain the handle 204 in a distal position.

According to an embodiment herein, the proximally directed spring force applied to the handle 204 by the resilient feature 242 may aid in locking the handle 204 in a distal position with the locking feature 244. As discussed above, the resilient feature 242 may urge the handle 204 proximally. Once the handle 204 has been engaged with the locking feature 244, the proximal force on the handle 204 may maintain the handle 204 in locking engagement with the locking feature 244.

Figure 20:
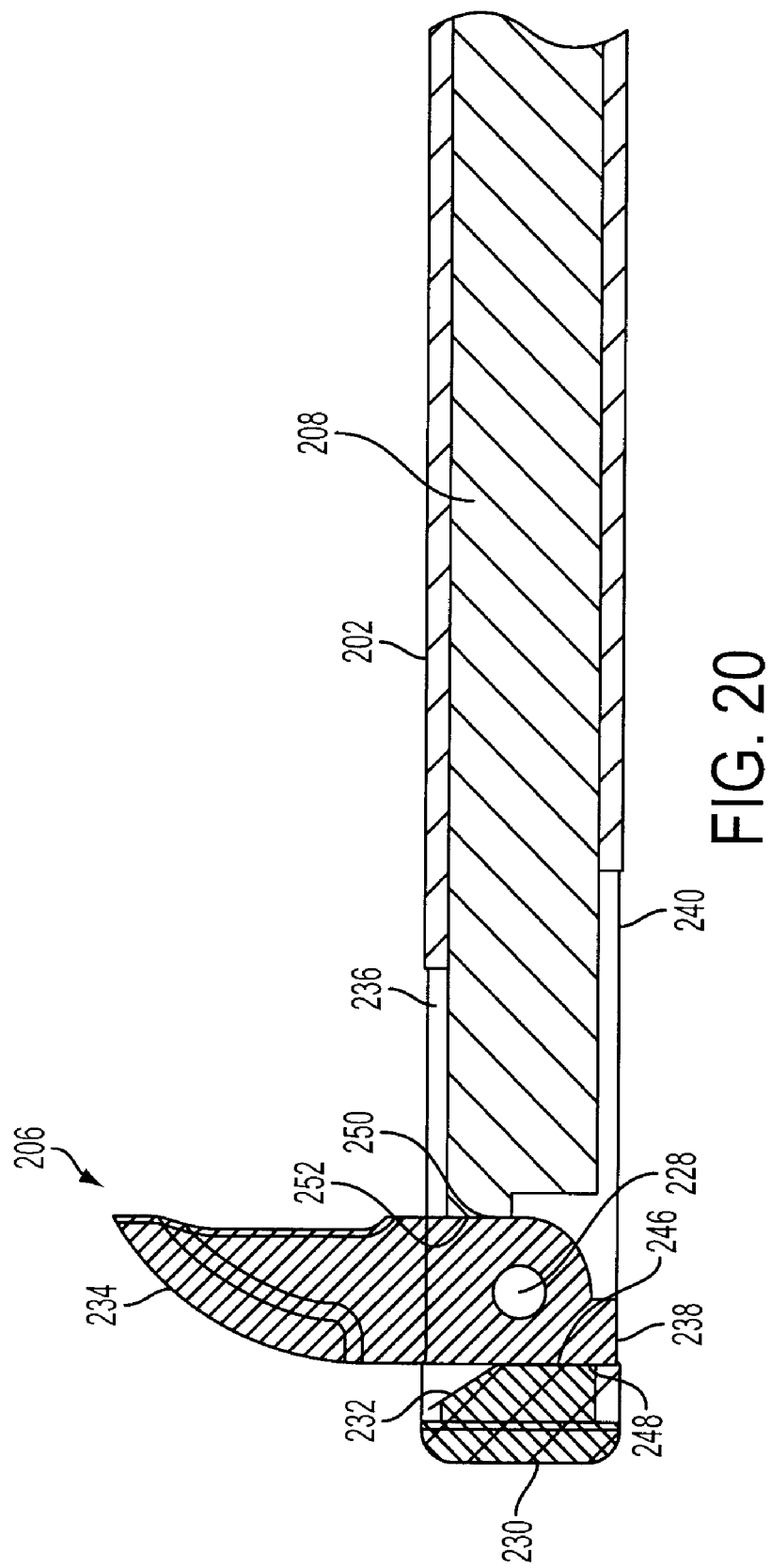
FIG. 20 is a detailed cross-sectional view of the distal end of the excision device of FIG. 14 with the cutter in a deployed configuration.

A detailed view of a cutter 206 according to the illustrated embodiment is shown in a deployed configuration in FIG. 20. As previously mentioned, the cutter 206 may be moved from a retracted or stowed configuration to a deployed configuration when the cutter 206 is moved distally by distal translation of the pushrod 208 within the shaft 202. The blade portion 234 of the cutter 206 may contact the surface 232 of the distal tip 230 of the excision device 200. The angled or arcuate geometry of the surface 232 and/or of the blade portion 234 may cause the cutter 206 to pivot outwardly through the slot 236 in the shaft 202 about a pivot axis 228.

As illustrated, when the cutter 206 is in a deployed configuration a straight tang portion 246 of the cutter 206 may contact a straight wall portion 248 of the distal tip 230, which may extend generally transverse to the axis of the shaft 202. Additionally, when the cutter 206 is in a deployed configuration, a distal end 250 of the pushrod 208 may bear against a generally flat region of the spine 252 of the cutter 206. In this manner, the cutter 206 may be secured between the distal tip 230 and the pushrod 208 in a deployed configuration.

Figure 21:
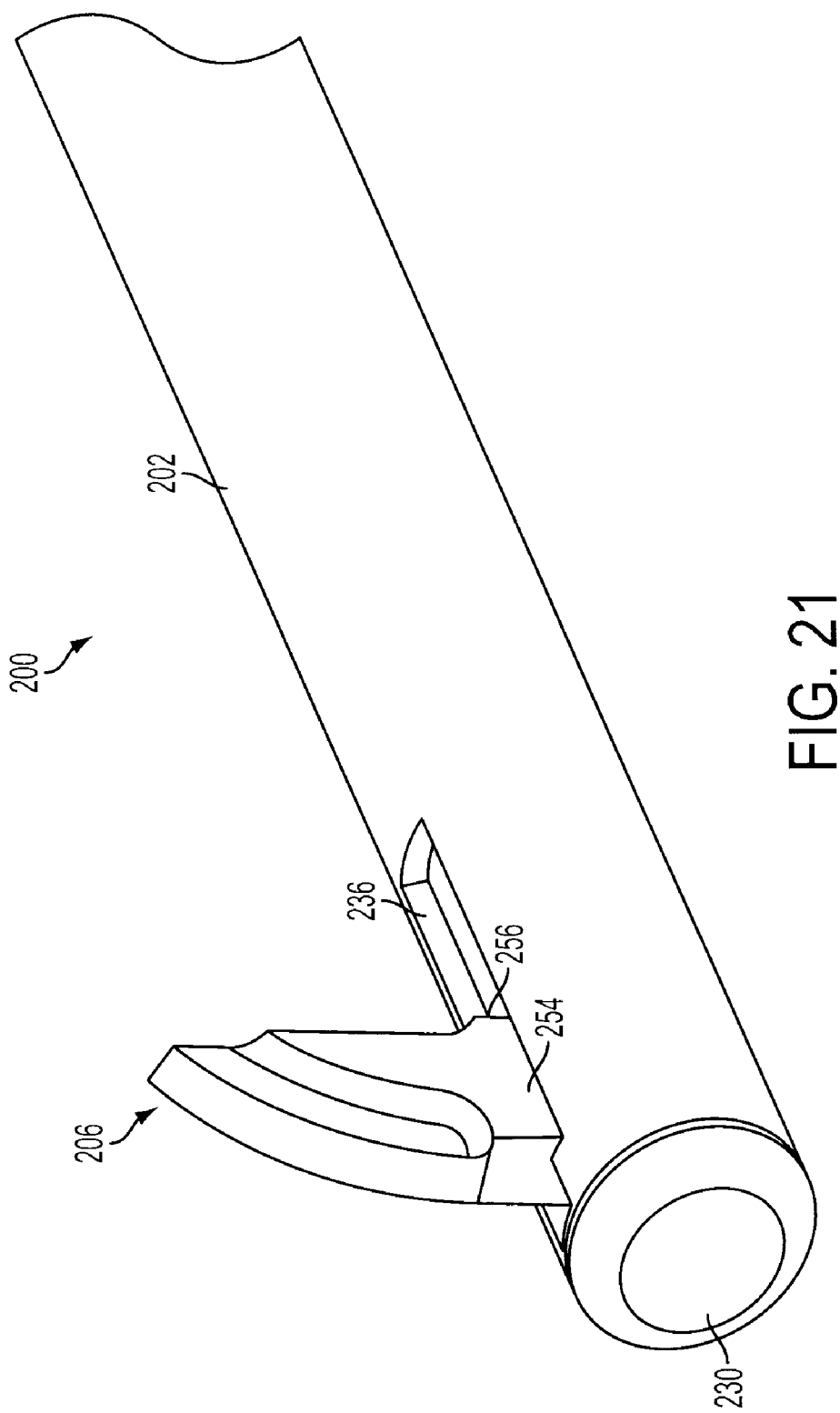
FIG. 21 is a detailed perspective view of the distal end of the excision device shown in FIG. 14 with the cutter in an extended configuration.

With additional reference to FIG. 21, when the cutter 206 is in a deployed configuration, the cutter 206 may resist wobbling and/or torsional loading. As depicted, the width of the cutter 206 may be closely tolleranced to the width of the slot 236. That is, the width of the cutter 206 may be such that the sides 254 of the cutter 206 may be in contact with, or closely spaced from, the side of the slot 236. Accordingly, a side loading of the cutter 206 may be transmitted to the shaft 202 as a torsional force, without substantial deflection or movement of the cutter 206. Similarly, the tab 238 of the cutter 206 may be closely tolleranced to the width of the slot 240 in the shaft 202. Supporting the cutter 206 on each side of the shaft 202 may allow the cutter 206 to resist side loading and/or wobbling around the axis of the shaft 202.

An excision device 200 consistent with the depicted embodiment of FIGS. 14-21 may be employed for excising at least a portion of an articular surface and/or at least a portion of underlying bone in a manner similar to the excision device previously described with reference to FIGS. 8 and 9. Specifically, the excision device 200 may be inserted extending at least partially through the sheath 54. According to one embodiment, extension of the excision device 200 through the sheath 54 may be controlled by observing the position of the distal tip 230 of the excision device 200 relative to the articular surface 40 to be excised. Observation of the position of the distal tip 230 relative to the articular surface 40 may be accomplished arthroscopically or using any suitable imaging or referencing systems.

When the excision device 200 has been positioned extending at least partially through the sheath 54 the shaft 202, and the cutter 206 and pushrod 208, may be rotationally driven within the sheath 54. According to one embodiment, the shaft 202, cutter 206, and pushrod 208 may be rotationally driven by a drive motor, such as a drill. The excision device 200 may be stabilized at the proximal end thereof by the handle 204, which may be maintained rotationally independent from the shaft 202 by the bearings 214, 216. The cutter 206 may be deployed from the shaft 202 by moving the handle 204 to a distal position, thereby also moving the pushrod 208 to a distal position. Movement of the pushrod 208 to a distal position may cause the cutter 206 to be deployed from the shaft 202 in the previously described manner. Once the cutter 206 has been fully deployed by moving the handle 204 to a distal position, the cutter 206 may be maintained in the deployed configuration by engaging the handle 204 with the locking feature 244.

Rotation of the shaft 202 with the cutter 206 in a deployed configuration may excise at least a portion of the articular surface 40 and/or the underlying bone 44. As the articular surface 40 and/or underlying bone 44 are being excised by the cutter 206, the excision device may be moved distally toward the sheath 54 until the cutter 206 contacts the distal end of the sheath 54. The cutter may include a shelf 256 on the proximal side, or spine, of the cutter 206. The shelf 256 may contact the distal end of the sheath 54, thereby preventing further withdrawal of the excision device 200. As discussed previously, sheath 54 may be positioned at a depth from the articular surface 40 to define a depth of an implant site created by excising at least a portion of the articular surface 40 and/or at least a portion of the underlying bone. The shelf 256 and/or the distal end of the sheath 54 may be formed to prevent and/or minimize the production of debris resulting from rotational contact between the cutter 206 and the sheath 54.

Figure 22:
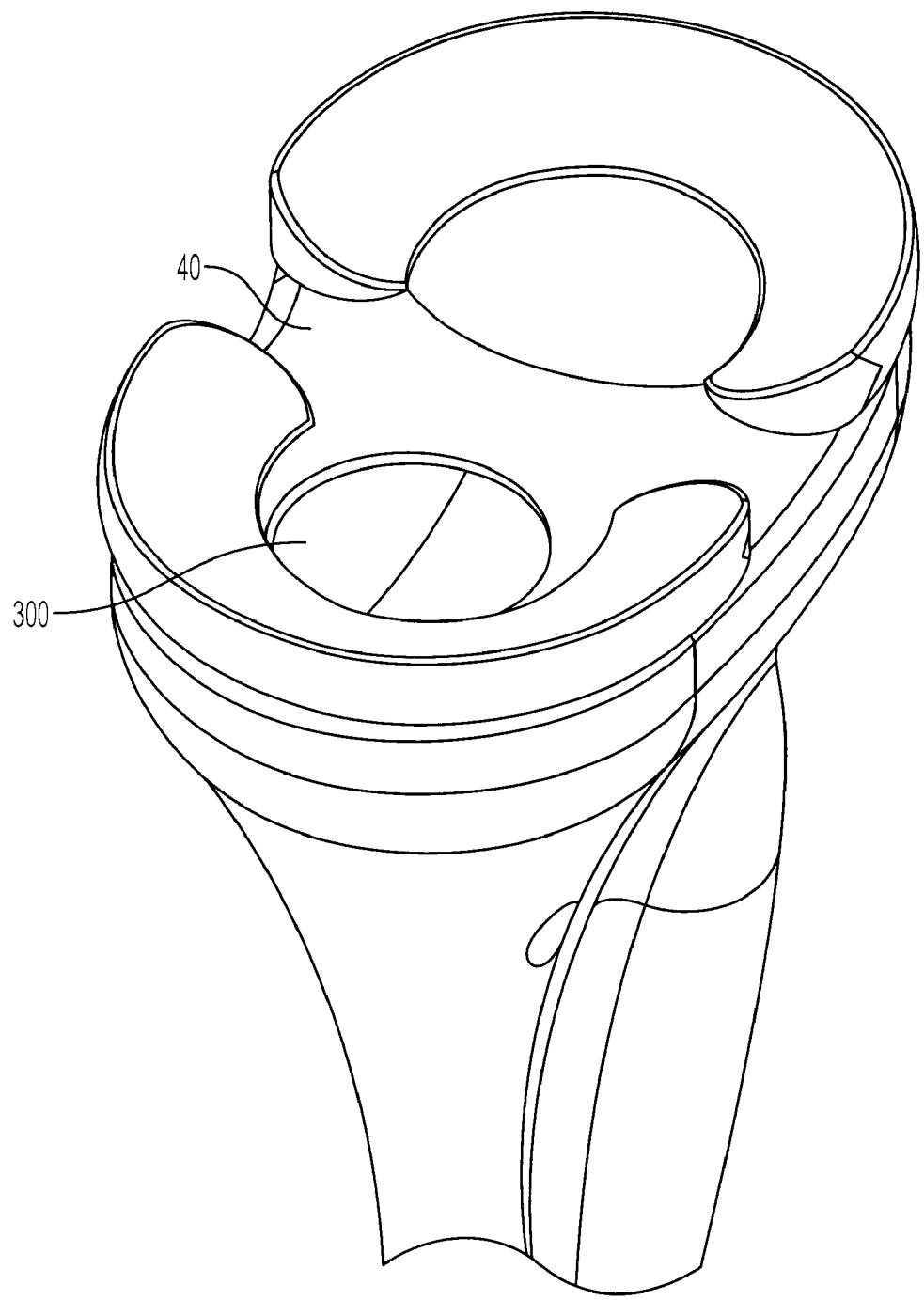
FIG. 22 is a perspective view of a tibial articular surface including an embodiment of an articular surface implant consistent with the present disclosure.
Figure 23:
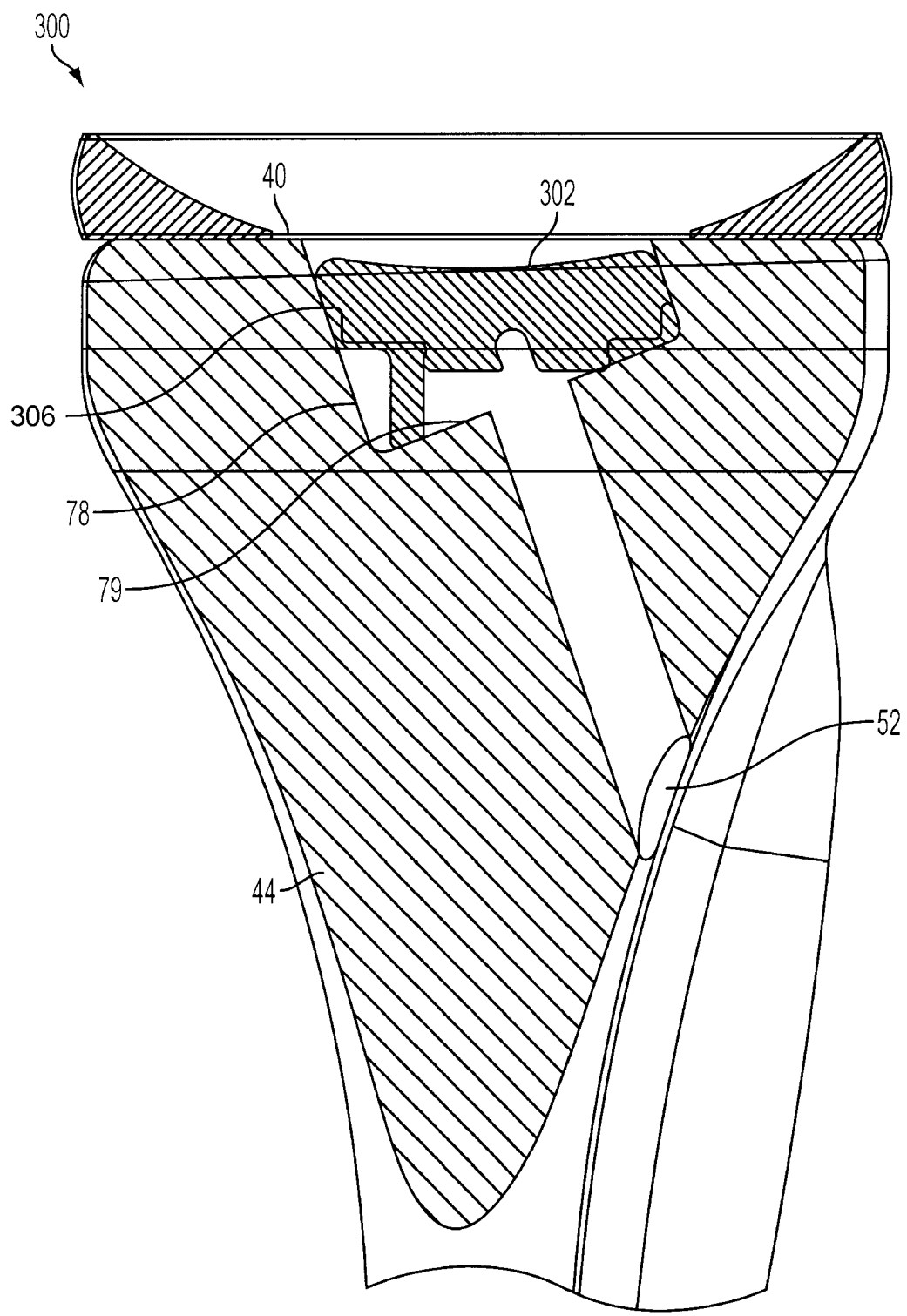
FIG. 23 is a cross-sectional view of a tibia including an embodiment of an articular surface implant consistent with the present disclosure.

Referring to FIG. 22, an articular surface 40 is illustrated in which a portion of the articular surface 40 includes an articular surface implant 300 consistent with the present disclosure. According to one embodiment, the implant 300 may be installed in an implant site 78, such as may be formed using a retrograde access system as described previously. The implant 300 may have a load bearing surface 302 that may replace at least a portion of the excised articular surface 40 of the bone 44. According to one embodiment, the load bearing surface 302 of the implant 300 may have a geometry that is based on the geometry or contour of the portion of the articular surface 40 being replaced. As used in any embodiment herein, a geometry of the load bearing surface based on the geometry of the articular surface 40 being replaced may mean that the geometry of the load bearing surface 302 may provide similar mechanical action in relation to a cooperating articular surface, soft tissue, etc during articulation of the joint.

Consistent with one embodiment herein, the geometry or curvature of the load bearing surface 302 of the implant 300 may be provided based on quantitative and/or qualitative reference to none, any, all, or any combination of the portion of the articular surface being replaced by the implant 300, the articular surface 40 receiving the implant, the geometry of a cooperating implant, and/or the geometry of a cooperating articular surface. As discussed previously, the geometry or contour of the portion of the articular surface 40 being replaced may be qualitatively and/or quantitatively determined using aiming tip 22 of the drill guide system 10. Various other methods for determining the geometry of the portion of the articular surface 40 being replaced may also be employed, including visual approximation.

With general reference to FIGS. 23 through 28, according to one embodiment an articular surface implant 300 consistent with the present disclosure may be provided as an assembly including an upper component 304 and a lower component 306. The upper component 304 may include the load bearing surface 302. The lower component 306 may be configured to be disposed within the implant site 78 and may be capable of seating against the bottom surface 79 of the implant site 78.

The lower component 306 may define a recess 308 capable of receiving at least a portion of the upper component 304. The lower component 306 may include a shelf feature 310 about at least a portion of the bottom region of the recess 308. The shelf feature 310 may be capable of supporting at least a portion of the bottom surface 312 of the upper component 304. Stresses and loads applied to the load bearing surface 302 of the upper component may be transferred through the bottom surface 312 of the upper component to the lower component at the shelf feature 310. Stresses and loads transferred to the lower component 306 at the shelf feature may be transferred to the bone 44 containing the implant 300 through the base 314 and/or sides 316 of the lower component 306.

The upper component 304 may additionally include a locking feature 318 extending from the bottom surface 312. The locking feature 318 may be capable of being coupled to the lower component 306 of the implant 300. As depicted, for example in FIGS. 26 and 27, the locking feature 318 may have an elongated shape. The lower component 306 may include a corresponding locking recess 320 capable of receiving the locking feature 318. The elongated geometry of the locking feature 318 and the locking recess 320 may facilitate aligning the upper component 304 with the lower component 306 and/or may reduce and/or prevent rotation of the upper component 304 relative to the lower component.

Figure 24:
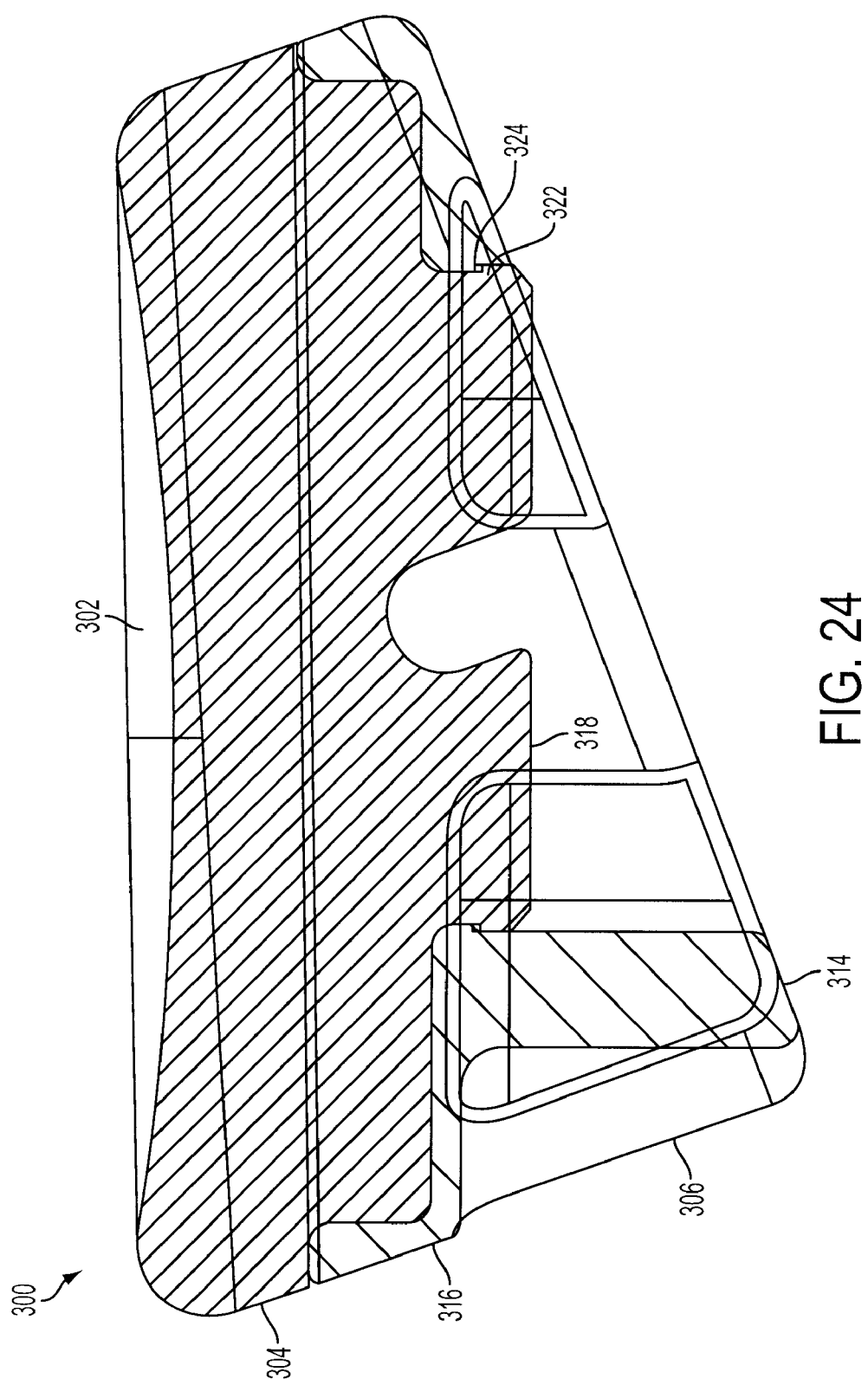
FIG. 24 is an enlarged cross-sectional view of an embodiment of an articular surface implant consistent with the present disclosure.
Figure 25:
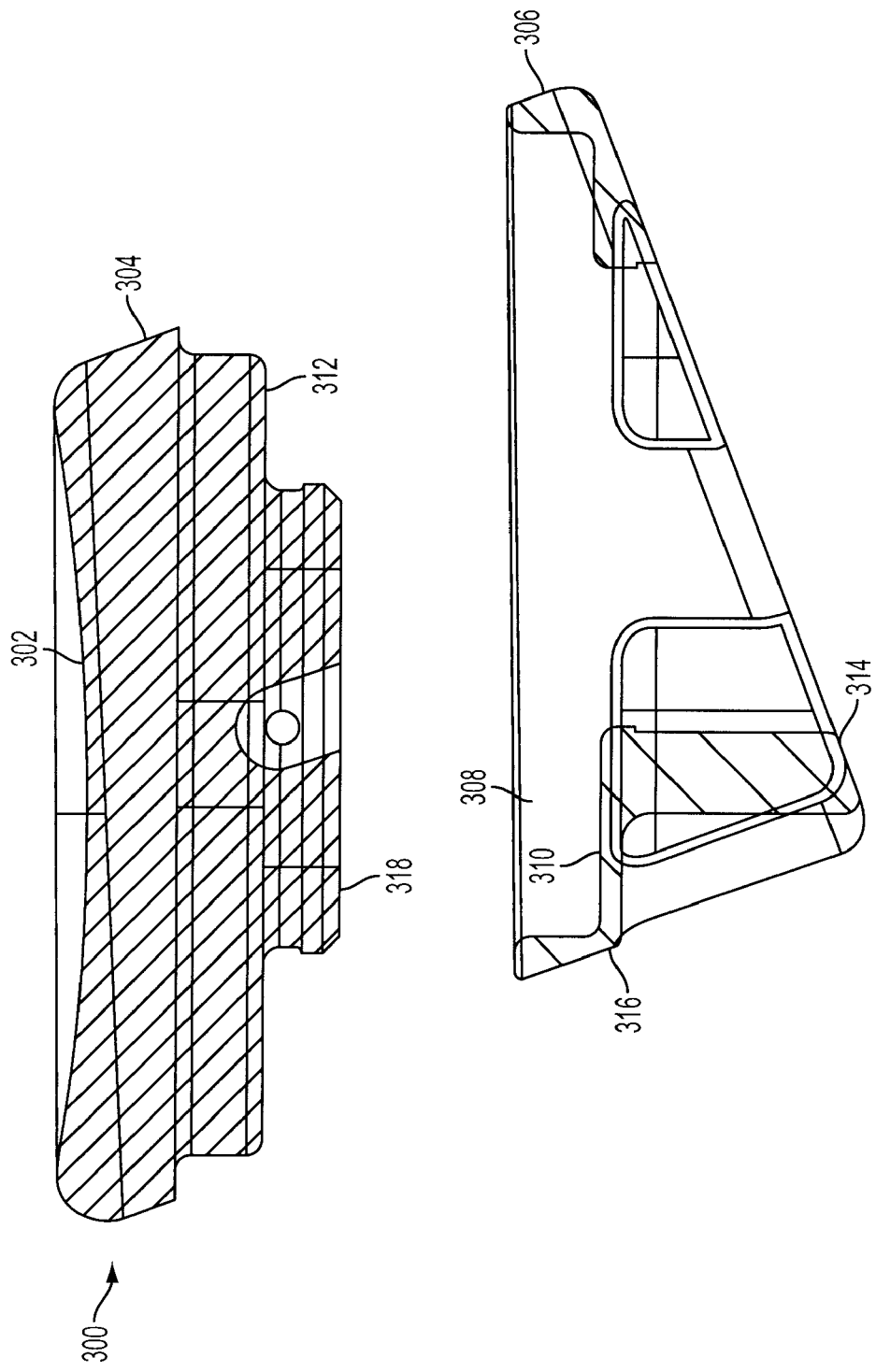
FIG. 25 is an exploded cross-sectional view of the articular surface implant depicted in FIG. 24.

As best depicted in FIG. 24, coupling of the upper component 304 and the lower component 306 may be at least in part achieved using cooperating protrusions 322 on the locking feature 318 of the upper component 304 and indentations, or undercuts, 324 on the lower component 306. Consistent with such an arrangement, the locking feature 318 of the upper component 304 may be pressed into the locking recess 320 of the lower component 320 resiliently deforming the locking feature 318 and or the locking recess 320 until the protrusions 322 of the locking feature 318 align with the indentations, or undercuts, 324 in the locking recess 320. When the protrusions 322 and indentations, or undercuts, 324 align with one another, the locking feature 218 and or the locking recess 320 may resiliently recover to provide locking engagement between the upper component 304 and the lower component 306. Various other cooperating features may additionally, or alternatively be employed for coupling the upper component 304 to the lower component 306.

Consistent with the retrograde access system disclosed herein, the retrograde access path may be oriented at an angle relative to the articular surface 40 and/or at an angle relative to a normal axis generally at the center of the excised region of the articular surface 40. As a result, the implant site 78 may generally have a circular cross-section that may be oriented at an angle relative to the articular surface 40. Consistent with such an embodiment, the angular intersection of the implant site 78 and the articular surface 40 may provide a generally oval or elliptical shape of the implant site 78 at the articular surface 40.

Consistent with the geometry of the implant site 78, the implant 300 may be generally provided having a cylindrical shape corresponding to the implant site 78. The shape of the load bearing surface 302 may generally be defined by the cylindrical geometry of the implant 300 bounded at the load bearing surface by a plane at an angle to the axis of the cylinder. The angle of the plane defining the shape of the load bearing surface 302 may generally correspond to the angle of the implant site 78 relative to a normal axis through the articular surface 40 at the center of the implant site 78. Accordingly, the load bearing surface 302 may have a generally elliptical or oval shape, as best observed in FIG. 27.

In addition to having an oval or elliptical shape, an implant 300 consistent with the foregoing description may have an angled profile along the longitudinal axis of the implant 300. In the illustrated embodiment, the upper component 304 of the implant is provided having a generally uniform height. In order to accommodate the geometry of the implant site 78, the lower component 306 of the implant 300 may be provided having an angled configuration, relative to the longitudinal axis thereof.

Figure 26:
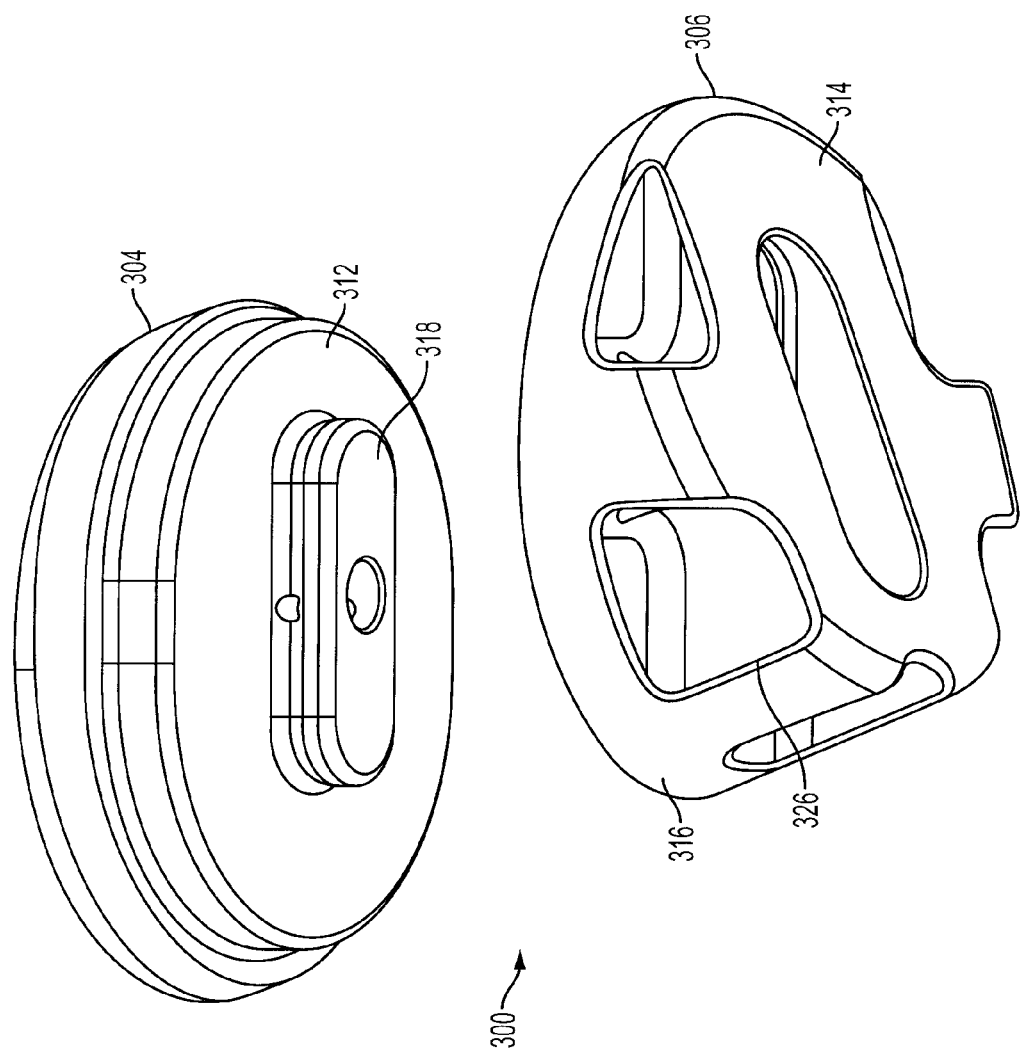
FIG. 26 is an exploded perspective view of the articular surface implant depicted in FIG. 24.
Figure 27:
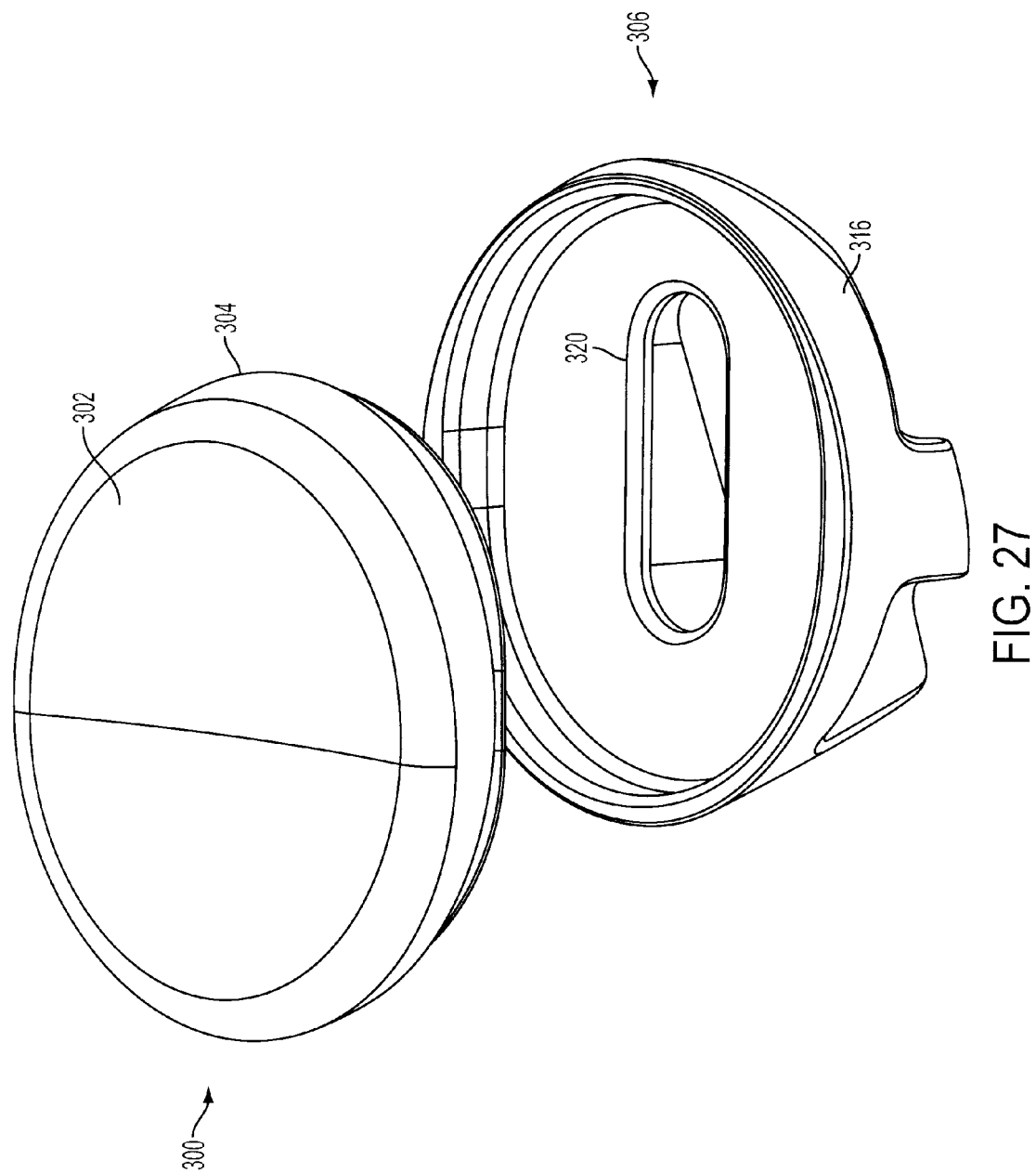
FIG. 27 is an exploded top perspective view of the articular surface implant depicted in FIG. 24.
Figure 28:
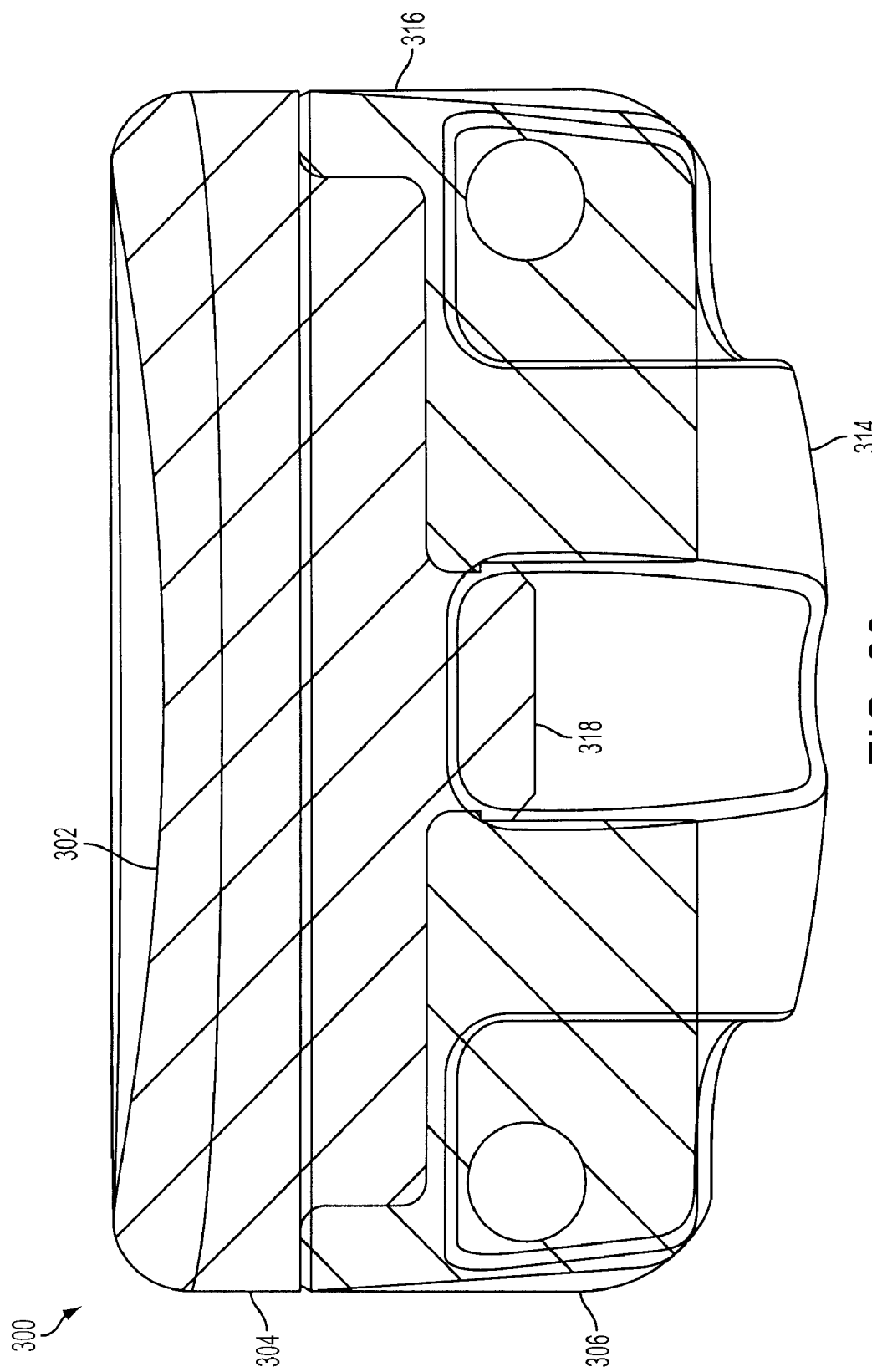
FIG. 28 is a cross-sectional view of an articular surface implant consistent with the present disclosure.

Turning to FIG. 26, as shown the sides 316 of the lower component may include cutouts 326. The cutouts 326 may reduce the amount of material of the lower component 306. The reduction in material afforded by the cutouts 326 may provided a corresponding reduction in the weight of the lower component. Additionally, the cutouts 326 may facilitate retention of the implant 300 in the implant site 78. For example, the cutouts 326 may allow the ingrowth of bone and/or mechanical coupling between the implant 300 and surrounding bone, e.g., using bone cement.

Referring to FIG. 29, another embodiment of a lower component 306a is illustrated. The lower component 306a may be formed generally as described with respect to the preceding embodiment, however, the lower component may include a projection 328 extending around at least a portion of the lower component 306. The projection 328 may facilitate anchoring the implant 300 in the implant site 78 formed in the bone 44. When the implant 300 is installed within the implant site 78 the projection 328 may engage the bone 44 around at least a portion of the circumference of the implant site 78. The projection 328 may dig into the bone 44 and resist extraction of the implant 300 from the implant site 78.

The implant 300 may be installed into the implant site 78 formed in the articular surface 40 by introducing the implant 300 into the implant site 78 from the articular surface 40. According to a first method, the lower component 306 may be at least partially inserted into the implant site 78 separately from the upper component 304. The lower component 306 may be introduced into the implant site 78 by urging the lower component 306 into the implant site 78 from the articular surface 40 of the bone. Alternatively, or additionally, a tether may be inserted through the retrograde access tunnel 52 and through at least a portion of the implant site 78. The tether may be coupled to the lower component 306 and the lower component 306 may then be pulled into the implant site 78 by withdrawing the tether through the access tunnel 52. According to either embodiment, the lower component 306 may be oriented relative to the implant site 78 and may be at least partially seated into the implant site, either from the articular surface 40 or through the access tunnel 52.

Bone cement and/or mechanical features may be used for securing the lower component 306 in position within the implant site 78. After the lower component 306 has been installed in the implant site 78, the upper component 304 may be installed into the implant site 78 and into the lower component 306. The locking feature 318 of the upper component 304 may be oriented and aligned with the locking recess 320 in the lower component 306. The upper component 304 may then be seated in the implant site 78 with the locking feature 318 of the upper component 304 coupled to the locking recess 320 of the lower component 306. As with installation of the lower component 306, the upper component 304 may be pressed or urged into the implant site 78 and/or into engagement with the lower component 306 by applying a force on the load bearing surface 302 of the upper component 304. Alternatively, or additionally, a rigid and/or flexible tether may be coupled to the upper component 304. The upper component 304 may then be urged into the implant site 78 and/or into engagement with the lower component 306 by pulling the tether through access tunnel 52 formed in the bone 44.

Consistent with an alternative embodiment, the upper component 304 may be assembled to the lower component 306 prior to installation of the implant 300 into the implant site 78. The locking feature 318 of the upper component 304 may be inserted into the locking recess 320 of the lower component 306 to assembly the implant 300. The assembled implant 300 may then be installed in the implant site 78. Similar to the preceding method, the implant 300 may be pressed into the implant site 78 by applying a force or impact to the load bearing surface 302 of the implant. Alternatively, or additionally, a rigid and/or flexible tether may be coupled to the implant 300. The implant 300 may then be urged into the implant site 78 by applying a force on the tether extending through the access tunnel 52 through the bone 44.

According to one aspect, the implant 300 including an assembly of an upper component 304 and a lower component 306 may allow the characteristics of the implant 300 to be customized. For example, the lower component 306 may be formed from a material that may provide strength and rigidity to support the upper component 304. Materials well known in the field of orthopedics may be used for the lower component 306. For example, stainless steel, titanium, cobalt-chromium alloys, etc. may be suitable for producing the lower component 306.

The upper component 304 and/or at least a portion of the upper component 304, for example a portion including the load bearing face 302, may be formed from biocompatible material that may provide any variety of desirable characteristics. For example, the upper component 304 may be selected to provide a low friction surface or to provide wear resistance. Additionally, the upper component 304 may include a material selected to provide at least some degree of shock absorption or cushioning effect. Suitable materials may include various polymeric materials, for example, high density polyethylene, ultrahigh molecular weight polyethylene, polyurethane, polyhydroxy-ethyl methacrylate gel, silicone, polyvinyl alcohol gel, etc. Ceramic materials, such as alumina or zirconia based materials, may also be used, e.g., to provide an inherent lubrication or low friction load bearing surface 302. Additionally, the upper component 304 may include materials that release or produce therapeutic or lubricating products and may even include biological materials. Those having skill in the art will appreciate numerous other materials that may be used to produce an upper component according to the present disclosure, including various metallic and/or composite materials. According to one embodiment, the upper component may be formed from a hydrogel material, for example a polyvinyl alcohol hydrogel material.

Consistent with the foregoing, according to one aspect a of the present disclosure a method is provided for replacing a portion of an articular surface. The method may include locating a portion of the articular surface and creating an access tunnel through bond behind the articular surface. The tunnel may be provided extending toward the articular surface. The method may further include installing a guide sheath at least partially in the access tunnel and excision at least a portion of the articular surface.

According to another aspect of the present disclosure, there may be provided an apparatus for excising a portion of an articular surface. The apparatus may include a drive shaft and a cutter that is capable of being engaged to the drive shaft. The cutter may be moveable between a first position extending from the drive shaft and a second position not extending from the drive shaft.

According to another aspect of the present disclosure, an implant may be provided. The implant may include an upper component having a load bearing surface for replacing a portion of an articular surface. The load bearing surface may have a geometry based on a geometry of the portion of the articular surface being replace. The upper component may further include an upper locking feature. The implant may also include a lower component that may be configured to be at least partially disposed in an implant site formed in the articular surface. The lower component may include a recess capable of receiving at least a portion of the upper component. The lower component may also include a lower locking feature which may be capable of engaging said locking feature of said upper component.

Various other features and advantages of the articular replacement system described herein will be appreciated by those having skill in the art. Similarly, the system disclosed herein is susceptible to numerous modifications and variations without materially departing from the spirit of the disclosure.

What is claimed is:

1. A system for creating an implant site on an articular surface of a bone comprising:
   a sheath comprising a generally tubular body defining a passageway extending along a longitudinal axis of said sheath from a proximal end to a distal end of said sheath, wherein at least a portion of an outer surface of said tubular body includes a threaded portion configured to engage with a tunnel extending within said bone such that said sheath is configured to provide positive alignment with a reference axis of said tunnel extending through said articular surface; and
   an excision device comprising:
      a shaft configured to be received through said proximal end of said sheath and to axially rotate within said passageway relative to said longitudinal axis of said sheath; and
      at least one cutter coupled to said shaft to axially rotate with said shaft relative to said longitudinal axis of said sheath to excise a least a portion of said articular surface in a retrograde manner as said at least one cutter is urged towards said distal end of said sheath, said at least one cutter having at least a portion of a cutting surface extending radially outwardly beyond an outer diameter of said generally tubular body of said sheath and a shelf configured to contact against said distal end of said sheath to control said depth of said implant site as said excision device is urged towards said distal end of said sheath in a retrograde manner.

2. The system of claim 1 wherein said sheath comprises a head disposed proximate a proximal end of said sheath.

3. The system of claim 2 wherein said head comprises an outer diameter greater than an outer diameter of said tubular body.

4. The system of claim 2 wherein said head is configured to engage with a driver for advancing said sheath with respect to said bone.

5. The system of claim 4 wherein said head comprises a socket configured to engage with and transmit torque from a driver head of said driver.

6. The system of claim 5 wherein said driver comprises a shaft configured to extend through at least a portion of said sheath.

7. The system of claim 4, wherein said head further includes a socket comprising a shoulder configured to allow said drive head to positively seat in said socket.

8. The system of claim 1 wherein an outer diameter of said tubular body and a pitch of said threaded portion are configured to facilitate alignment of said sheath with an axis of said tunnel.

9. The system of claim 1 wherein a distal end of said sheath comprises a taper configured to facilitate alignment of said sheath with a tunnel extending within said bone.

10. The system of claim 1, wherein said shelf comprises a generally flat profile.

11. The system of claim 1, wherein said shelf comprises a generally relieved profile.

12. The system of claim 1, wherein said shelf comprises a generally rounded profile.

13. The system of claim 1 further comprising a driver comprising a driver head configured to transmit torque to said sheath to advance said sheath within said tunnel towards said articular surface, said driver also comprising a shaft configured to be received within said passageway, wherein at least a portion of said shaft is configured to extend a predetermined distance beyond said distal end of said sheath, said predetermined distance substantially corresponding to said depth of said implant site.

14. The system of claim 1, wherein said distal end of said sheath is configured to be received a predetermined distance from said articular surface within a tunnel generally extending from said bone to said articular surface, said predetermined distance generally corresponding to a depth of said implant site.

15. The system of claim 14, wherein an outer opening of said tunnel comprises a taper configured to facilitate alignment of said sheath with said tunnel.

16. The system of claim 14, wherein said sheath is configured to engage with a driver for advancing said sheath within said tunnel.

* * * * *

UNITED STATES PATENT AND TRADEMARK OFFICE
CERTIFICATE OF CORRECTION

PATENT NO.       : 7,914,545 B2                                   Page 1 of 1
APPLICATION NO.  : 11/326133
DATED            : March 29, 2011
INVENTOR(S)      : Steven W. Ek It is certified that error appears in the above-identified patent and that said Letters Patent is hereby corrected as shown below:

In column 21, line 20, in Claim 1, delete "a least" and insert -- at least --, therefor.

Signed and Sealed this
Thirty-first Day of May, 2011

David J. Kappos
*Director of the United States Patent and Trademark Office*